(12) United States Patent  (10) Patent No.: US 11,644,117 B2
Kaiya                      (45) Date of Patent:     May 9, 2023

(54) VALVE STRUCTURE

(71) Applicant: ADVANCE DENKI KOGYO KABUSHIKI KAISHA, Kasugai (JP)

(72) Inventor: Naoko Kaiya, Kasugai (JP)

(73) Assignee: ADVANCE DENKI KOGYO KABUSHIKI KAISHA, Kasugai (JP)

( * ) Notice: Subject to any disclaimer, the term of this patent is extended or adjusted under 35 U.S.C. 154(b) by 194 days.

(21) Appl. No.: 17/140,727

(22) Filed: Jan. 4, 2021

(65) Prior Publication Data

US 2021/0207729 A1 Jul. 8, 2021

(30) Foreign Application Priority Data

Jan. 8, 2020 (JP) .............................. JP2020-001248

(51) Int. Cl.
*F16K 27/00* (2006.01)
*A61M 39/22* (2006.01)

(52) U.S. Cl.
CPC .......... *F16K 27/003* (2013.01); *A61M 39/223* (2013.01)

(58) Field of Classification Search
CPC ........... Y10T 137/87885; F16K 27/003; F15B 13/0817; F15B 13/0871
See application file for complete search history.

(56) References Cited

U.S. PATENT DOCUMENTS 5,983,933 A * 11/1999 Ohmi .................. F15B 13/0896
                                                        137/613
5,992,463 A * 11/1999 Redemann ............ C23C 16/455
                                                        137/884
6,012,479 A * 1/2000 Fukushima ........... F16K 27/003
                                                        137/271

(Continued)

FOREIGN PATENT DOCUMENTS

JP    H10-292871 A   11/1998
JP    2001-182860 A   7/2001

(Continued)

*Primary Examiner* — Kevin R Barss
(74) *Attorney, Agent, or Firm* — Kratz, Quintos & Hanson, LLP

(57) ABSTRACT

[Object] It is an object of the present invention to provide a valve structure capable of fixing a first connecting port of a first valve box block and a second connecting port of a second valve box block to each other when the first valve box block, a first driving portion block, the second valve box block and a second driving portion block are fixed to each other by bolts.

[Solving means] A first valve box bolt insertion hole 113 is formed in the first valve box block 110, a first driving portion bolt fixing hole 123 is formed in the first driving portion block 120, a second valve box bolt insertion hole 213 is formed in the second valve box block 210, and a second driving portion bolt fixing hole 223 is formed in the second driving portion block 220. The first valve box block 110 and the first driving portion block 120 are fixed to each other by a first bolt 130, the second valve box block 210 and the (Continued)

second driving portion block 220 are fixed to each other by a second bolt 230, and the first connecting port 111 and the second connecting port 211*a*, 211*b* are fixed to each other by a clamp member 10.

12 Claims, 13 Drawing Sheets

(56) References Cited

U.S. PATENT DOCUMENTS

| | | | | |
|---|---|---|---|---|
| 6,152,175 | A * | 11/2000 | Itoh | F16K 27/003 137/884 |
| 6,192,932 | B1 * | 2/2001 | Izumo | F16K 11/20 251/63.5 |
| 6,260,581 | B1 * | 7/2001 | Hollingshead | F16K 27/003 137/271 |
| 6,283,155 | B1 * | 9/2001 | Vu | F16K 27/003 137/884 |
| 6,640,835 | B1 * | 11/2003 | Rohrberg | F16K 27/003 285/125.1 |
| 7,213,618 | B2 * | 5/2007 | Milburn | F16K 27/003 137/884 |
| 8,061,385 | B2 * | 11/2011 | Kaitsuka | F16K 27/003 285/364 |
| 8,307,854 | B1 * | 11/2012 | Vu | F16K 27/003 137/884 |
| 2005/0081931 | A1 * | 4/2005 | Dezso | F15B 13/0814 137/884 |

FOREIGN PATENT DOCUMENTS

| | | |
|---|---|---|
| JP | 2002-276837 A | 9/2002 |
| JP | 2004-76787 A | 3/2004 |
| WO | WO-2006130774 A1 * 12/2006 | ........... F16K 27/003 |

* cited by examiner

[Fig. 1]
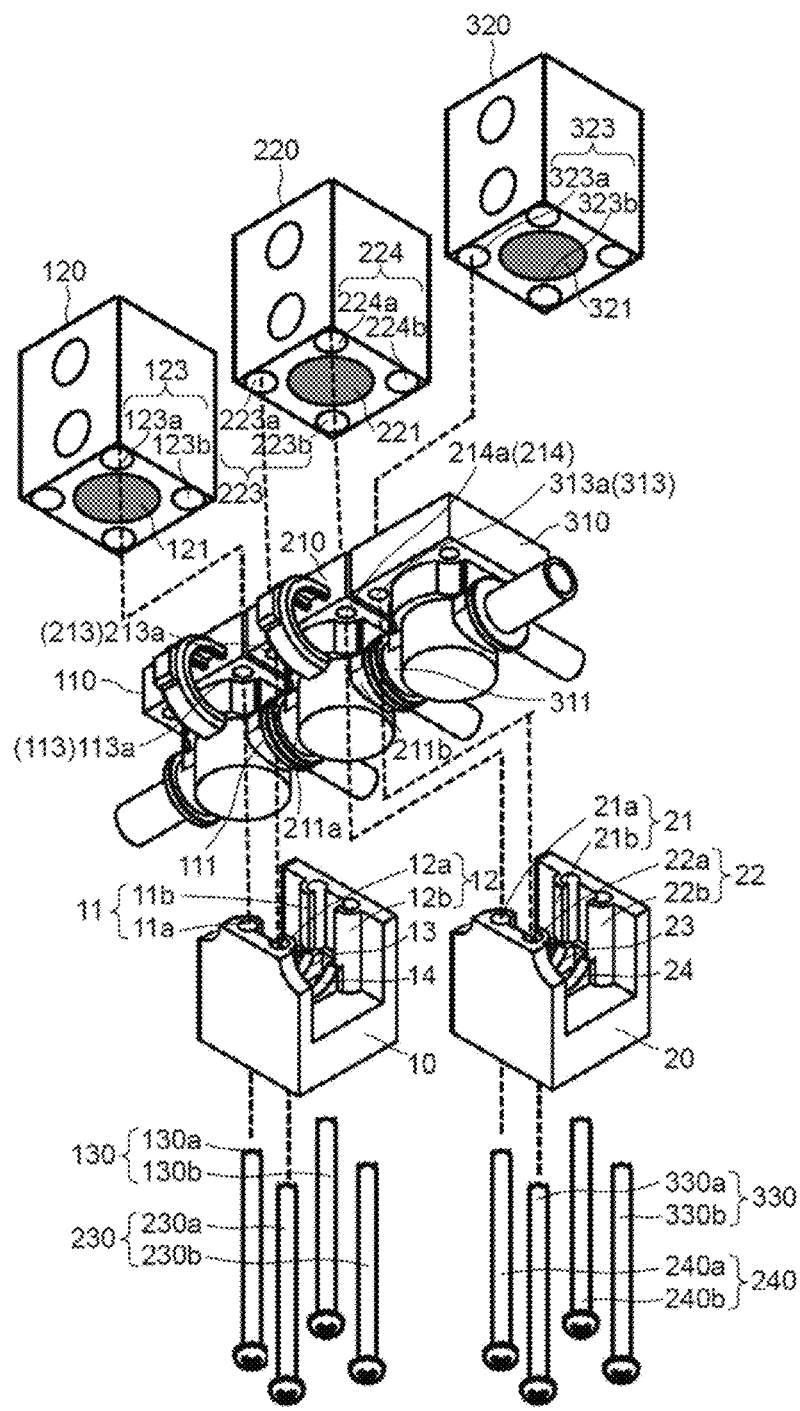

[Fig. 2]
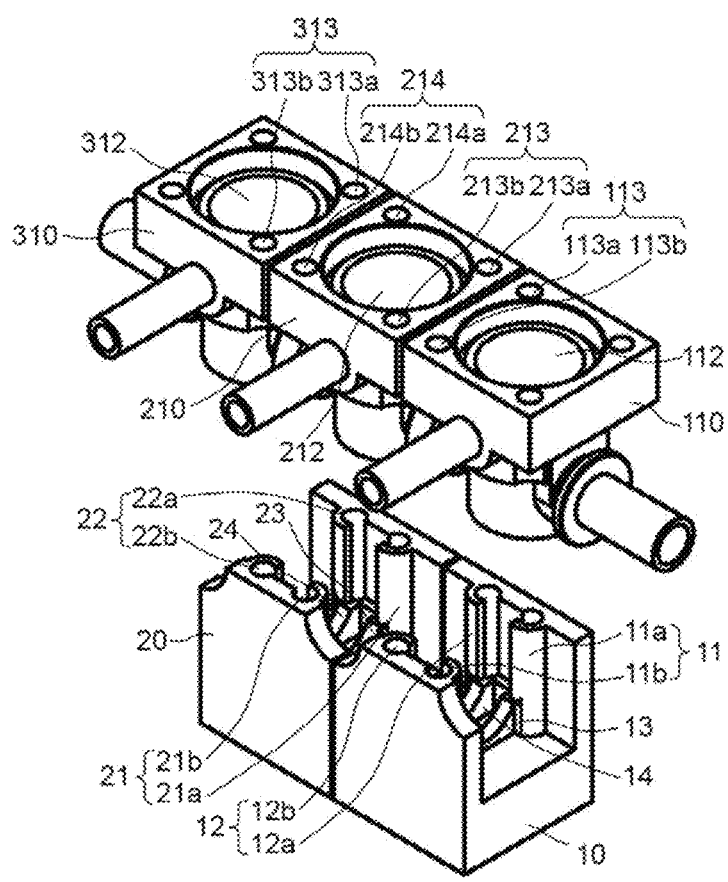

[Fig. 3]
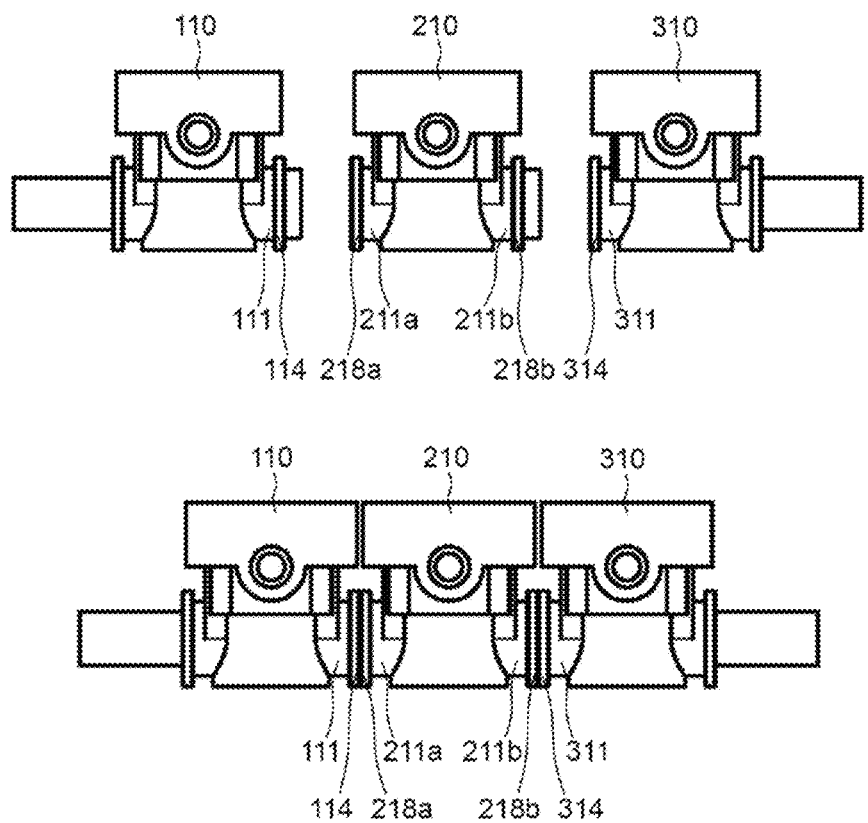

[Fig. 4]
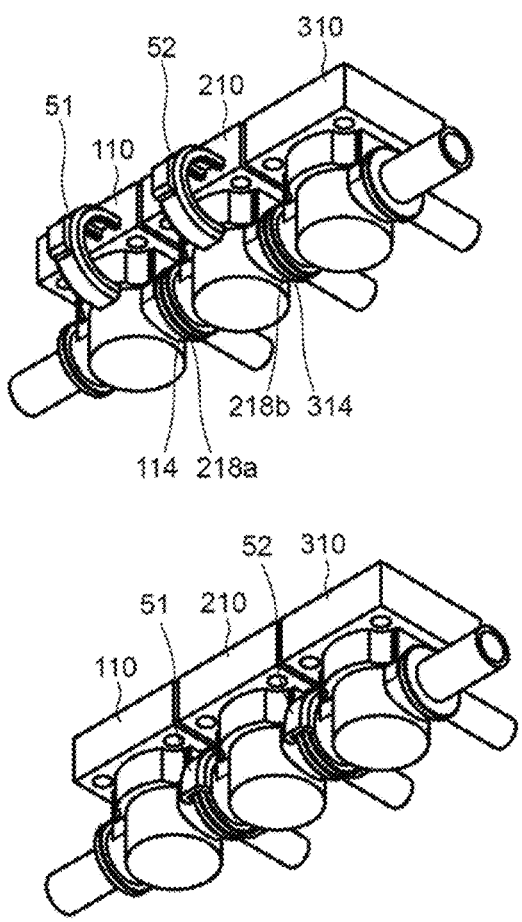

[Fig. 5]
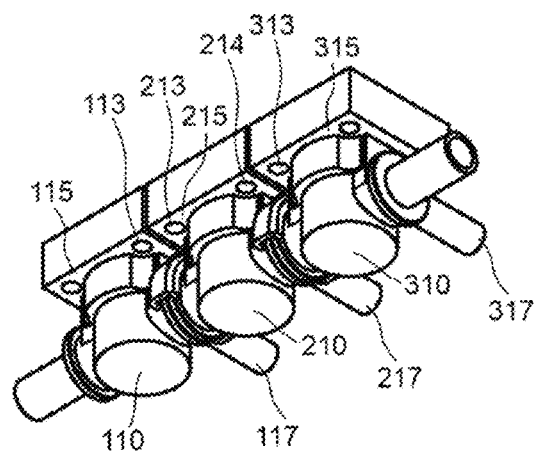
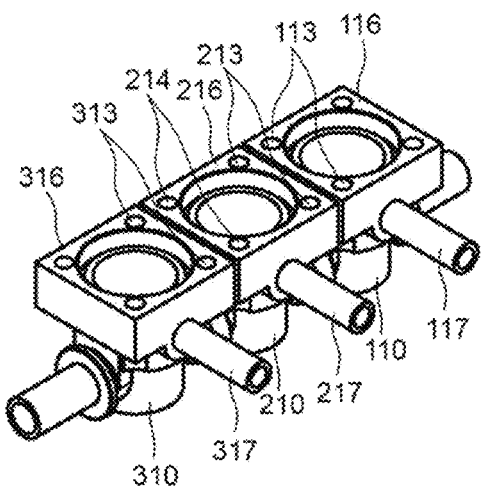

[Fig. 6]
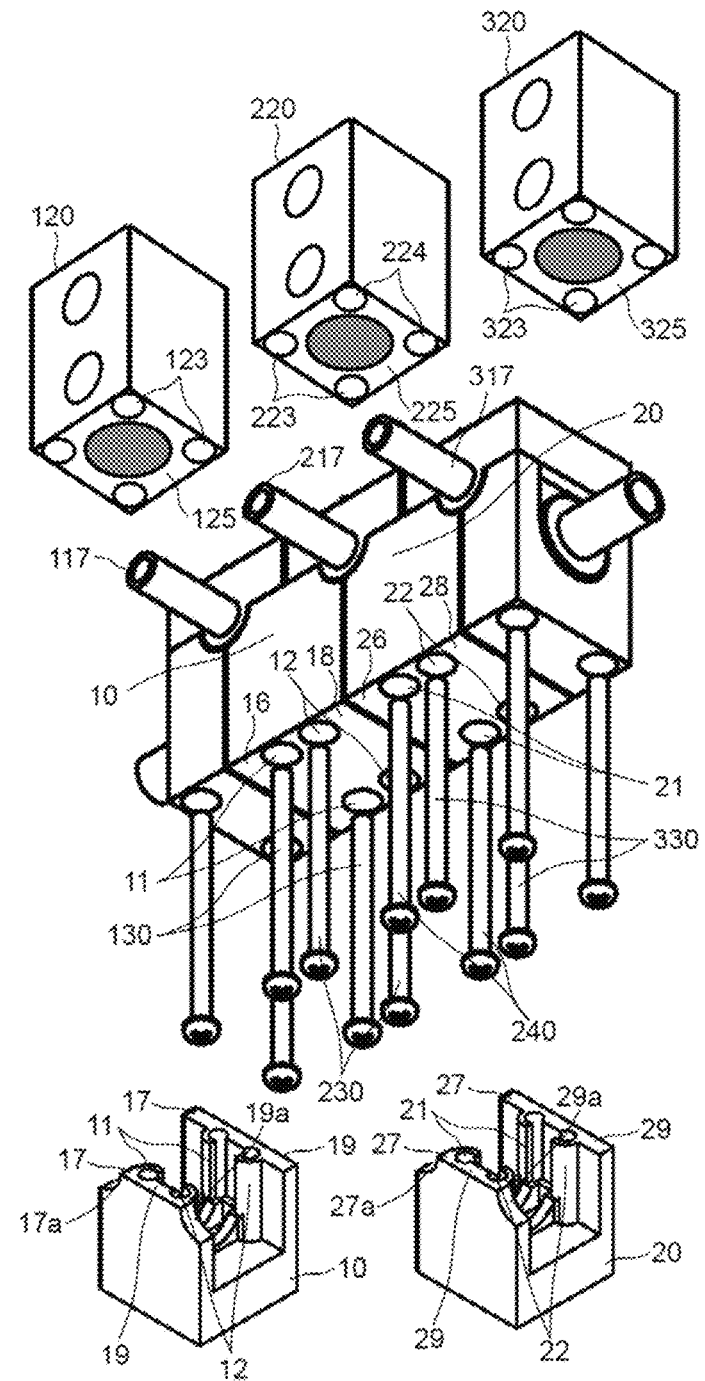

[Fig. 7]
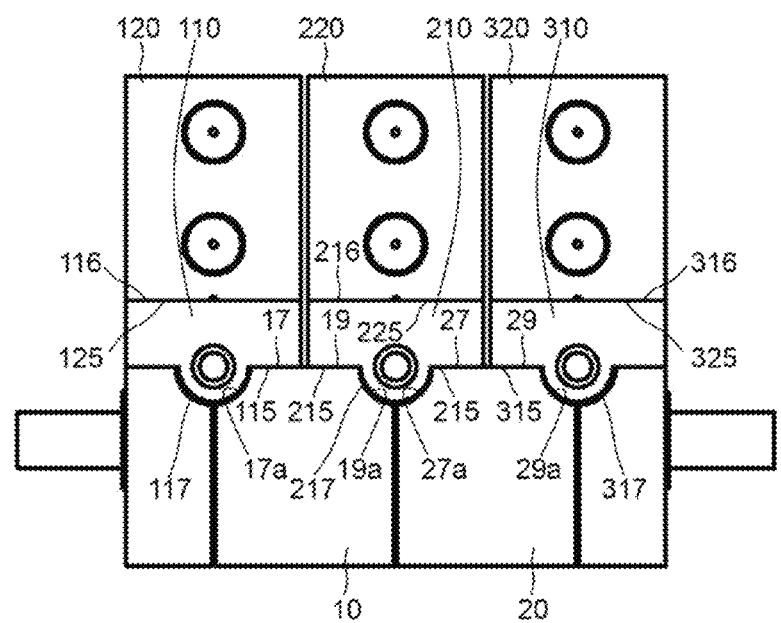

[Fig. 8]
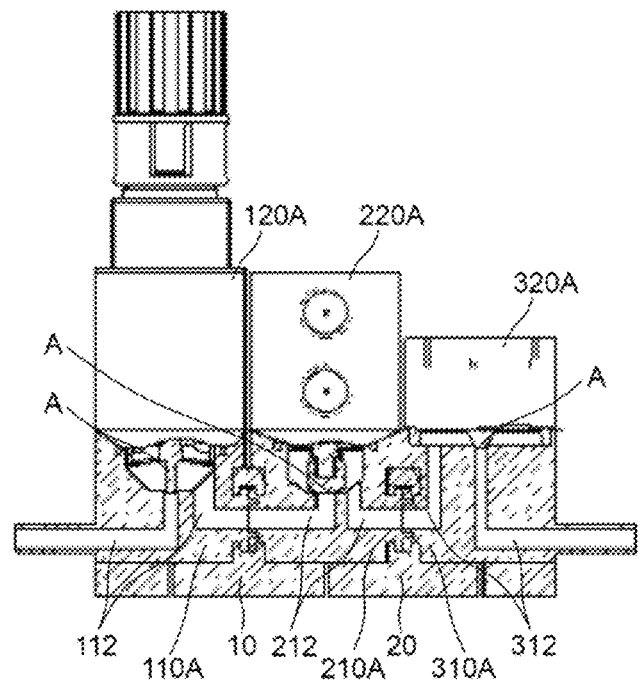

[Fig. 9]
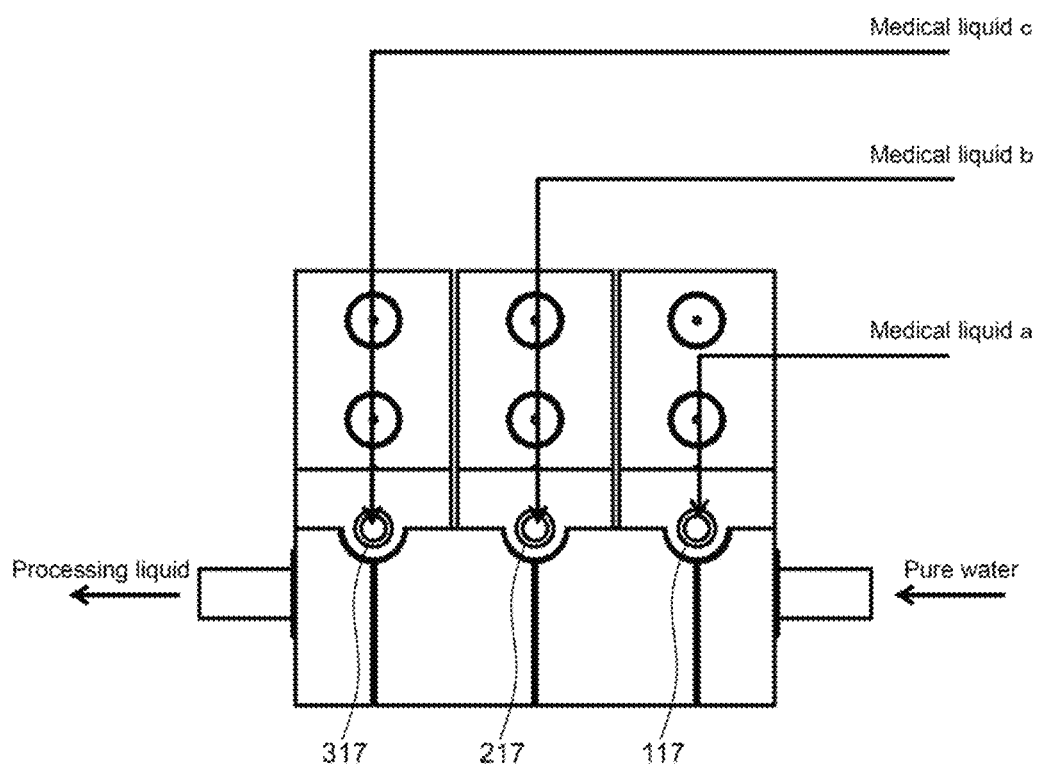

[Fig. 10]
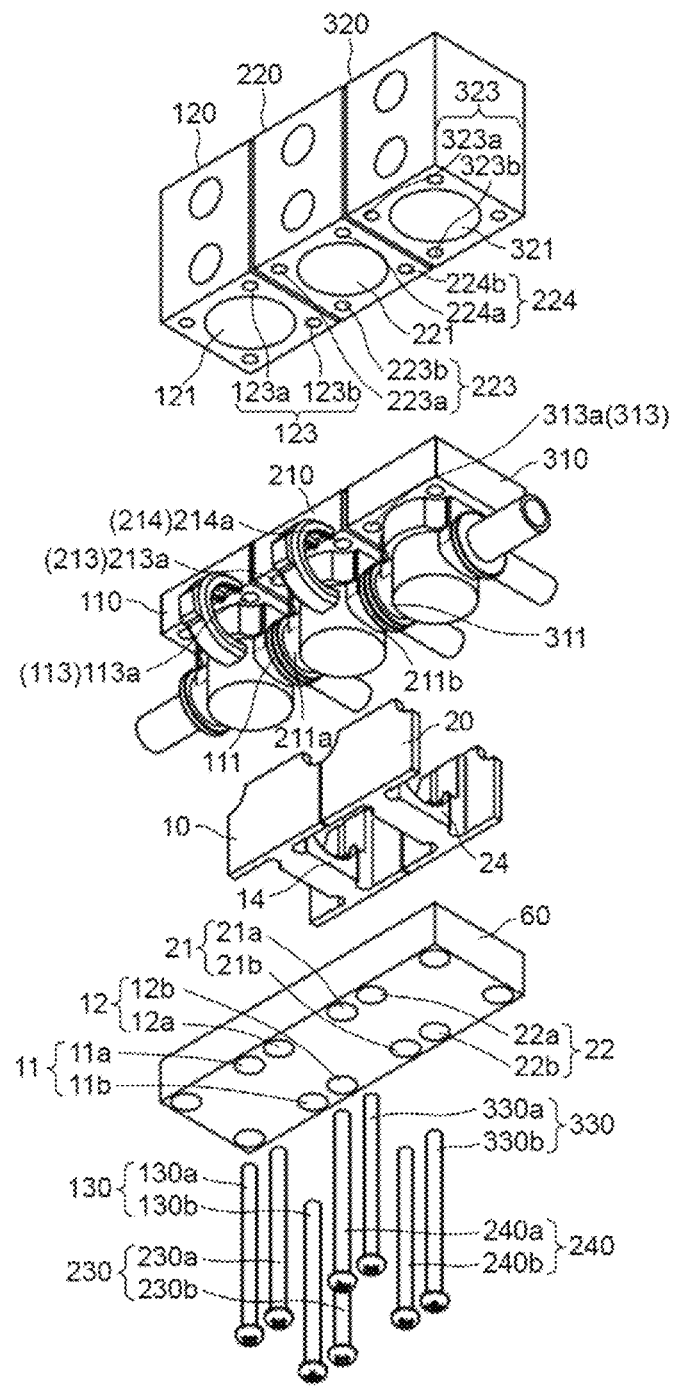

[Fig. 11]
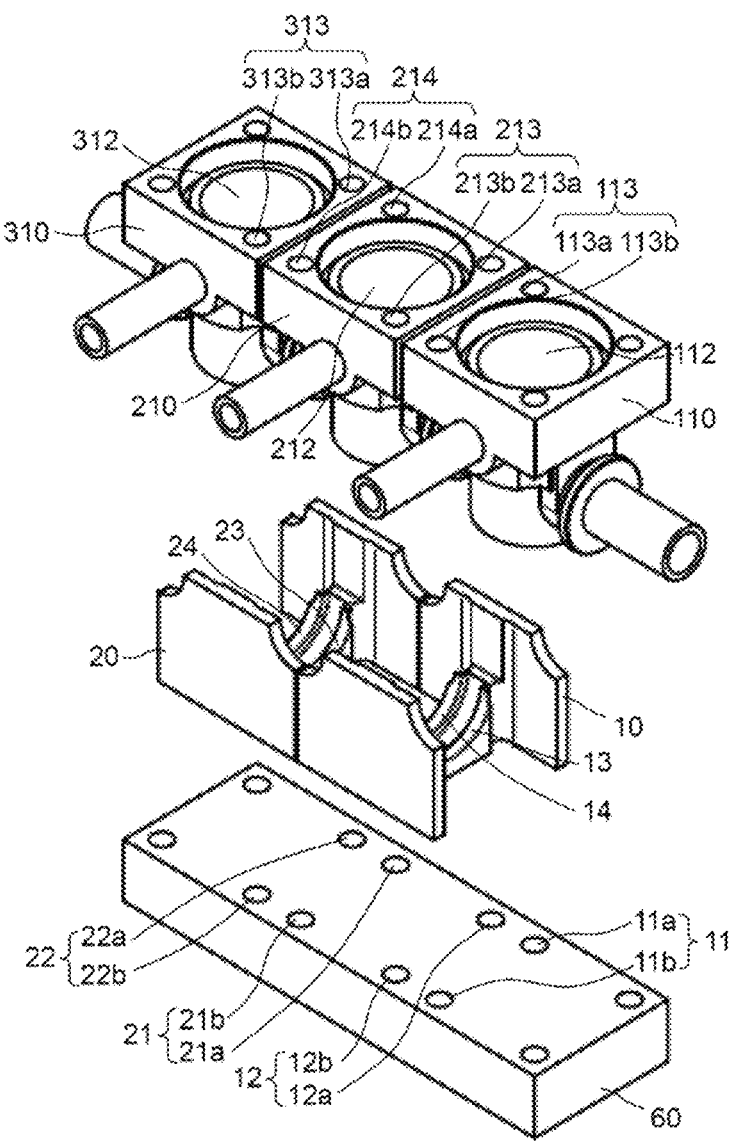

[Fig. 12]
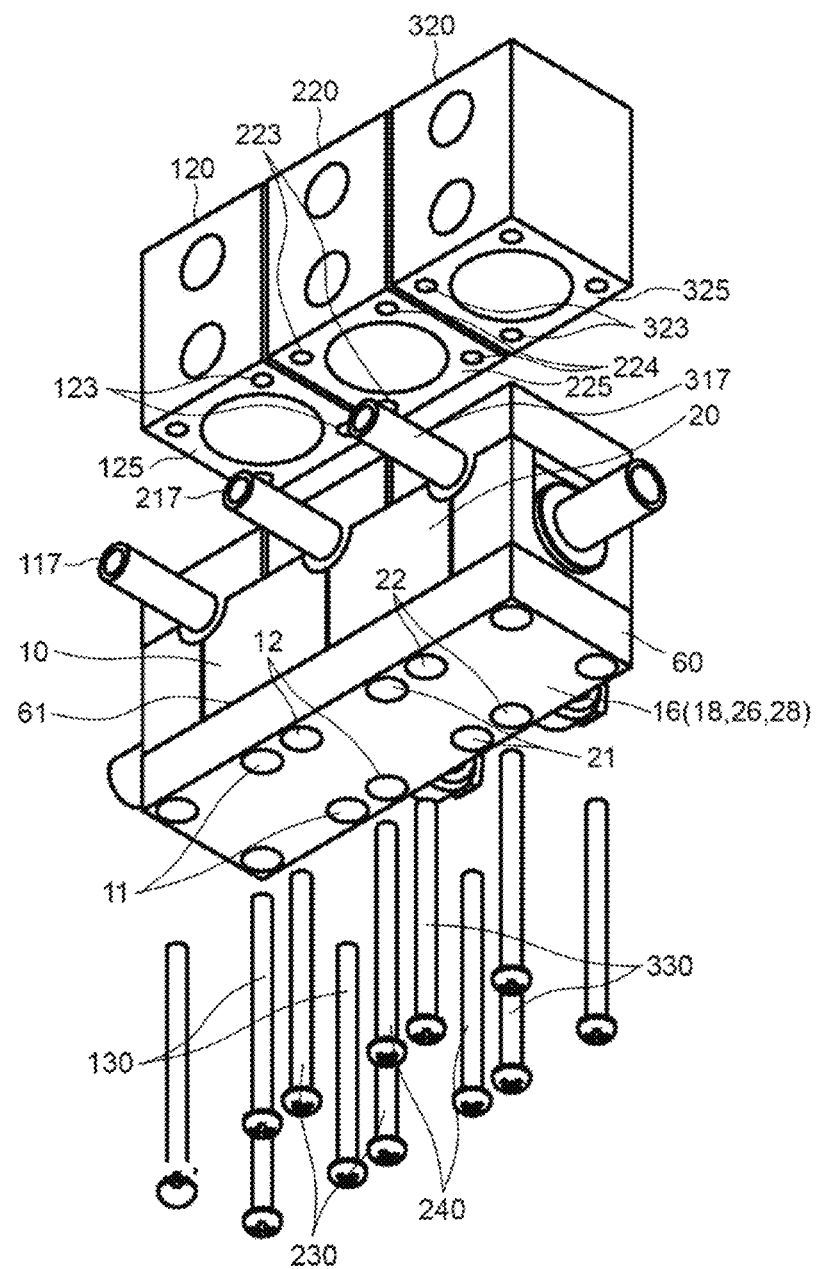

[Fig. 13]
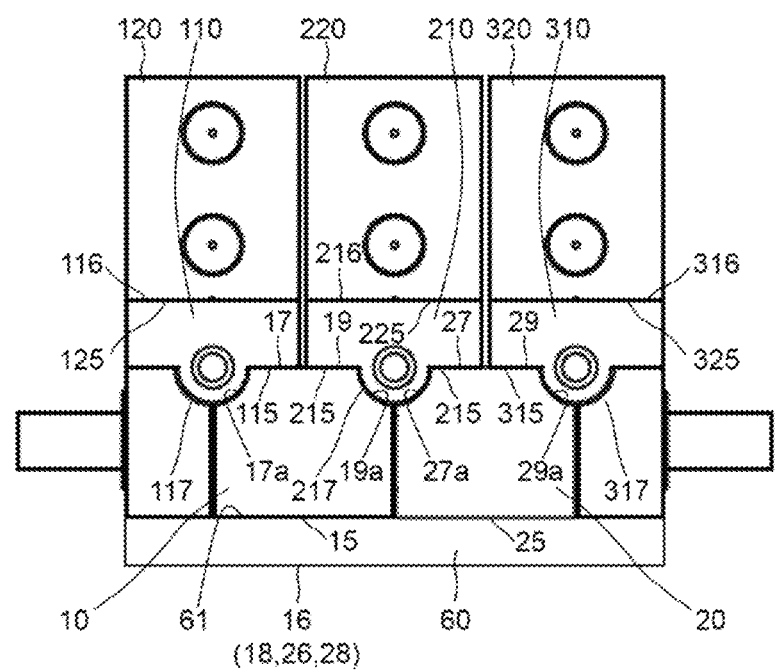

VALVE STRUCTURE

TECHNICAL FIELD

The present invention relates to a valve structure.

BACKGROUND TECHNIQUE

For example, patent documents 1 to 4 propose valve structures capable of supplying different fluids by switching between a plurality of flow path ports.

PRIOR ART DOCUMENTS

Patent Documents

[Patent Document 1] Japanese Patent Application Laid-open No. H10-292871
[Patent Document 2] Japanese Patent Application Laid-open No. 2001-182860
[Patent Document 3] Japanese Patent Application Laid-open No. 2002-276837
[Patent Document 4] Japanese Patent Application Laid-open No. 2004-76787

SUMMARY OF THE INVENTION

Problem to be Solved by the Invention

Each of the valve structures proposed by the patent documents 1 to 4 does not fix, through a bolt to each other, a valve box block provided therein with a flow path and a valve body which opens and closes the flow path, and a driving portion block provided therein with a valve body operating member which operates the valve body.

Further, according to patent document 1, a single valve box block includes a plurality of valve bodies, and a plurality of valve box blocks are not connected.

According to patent document 2, the valve structure is composed of a plurality of blocks, but the blocks are not fixed to each other through a bolt, and a clamp member is not used.

According to patent document 3, the valve box block and the driving portion block are integrally formed as a valve block body, and the valve block body is mounted on a common base member.

According to patent document 4, a single valve box block includes a plurality of valve bodies like patent document 1, and a plurality of valve box blocks are not connected.

It is an object of the present invention to provide a valve structure capable of fixing a first connecting port of a first valve box block and a second connecting port of a second valve box block to each other when the first valve box block and a first driving portion block are fixed to each other through a bolt and the second valve box block and a second driving portion block are fixed to each other through a bolt.

Means for Solving the Problem

An invention described in claim 1 provides a valve structure including: a first valve box block 110 in which a first flow path 112 is formed and a first valve body A for opening and closing the first flow path 112 is placed; a first driving portion block 120 provided therein with a first valve body operating member 121 which operates the first valve body A; a second valve box block 210 in which a second flow path 212 is formed and a second valve body A for opening and closing the second flow path 212 is placed; a second driving portion block 220 provided therein with a second valve body operating member 221 which operates the second valve body A; a first connecting port 111 projecting from the first valve box block 110; and a second connecting port 211a, 211b projecting from the second valve box block 210; in which the first flow path 112 and the second flow path 212 are brought into communication with each other by connecting the first connecting port 111 and the second connecting port 211a, 211b to each other, wherein a first valve box bolt insertion hole 113 into which a first bolt 130 is inserted is formed in the first valve box block 110, a first driving portion bolt fixing hole 123 into which the first bolt 130 is inserted to fix the first bolt 130 is formed in the first driving portion block 120, a second valve box bolt insertion hole 213 into which a second bolt 230 is inserted is formed in the second valve box block 210, a second driving portion bolt fixing hole 223 into which the second bolt 230 is inserted to fix the second bolt 230 is formed in the second driving portion block 220, the first valve box block 110 and the first driving portion block 120 are fixed to each other by the first bolt 130, the second valve box block 210 and the second driving portion block 220 are fixed to each other by the second bolt 230, and the first connecting port 111 and the second connecting port 211a, 211b are fixed to each other by a clamp member 10.

According to an invention described in claim 2, in the valve structure of claim 1, a first bolt holding portion 11 into which the first bolt 130 is inserted to hold the first bolt 130, and a second bolt holding portion 12 into which the second bolt 230 is inserted to hold the second bolt 230 are formed on the clamp member 10, the clamp member 10 is fixed to the first valve box block 110 and the first driving portion block 120 by the first bolt 130, the clamp member 10 is fixed to the second valve box block 210 and the second driving portion block 220 by the second bolt 230, the valve structure further forms another first valve box bolt insertion hole 113, another first driving portion bolt fixing hole 123, another first bolt holding portion 11, another second valve box bolt insertion hole 213, another second driving portion bolt fixing hole 223, and another second bolt holding portion 12, the valve structure further comprises another first bolt 130 and another second bolt 230, one of the first bolts 130a is placed in one of the first valve box bolt insertion holes 113a, one of the first driving portion bolt fixing holes 123a, and one of the first bolt holding portions 11a, the other first bolt 130b is placed in the other first valve box bolt insertion hole 113b, the other first driving portion bolt fixing hole 123b, and the other first bolt holding portion 11b, one of the second bolts 230b is placed in one of the second valve box bolt insertion holes 213a, 213b, one of the second driving portion bolt fixing holes 223a, 223b and one of the second bolt holding portions 12a, 12b, and the other second bolt 240a, 240b is placed in the other second valve box bolt insertion hole 214a, 214b, the other second driving portion bolt fixing hole 224a, 224b, and the other second bolt holding portion 21a, 21b.

According to an invention described in claim 3, the valve structure of claim 1 further includes a holding plate material where a first bolt holding portion 11 into which the first bolt 130 is inserted to hold the first bolt 130 and a second bolt holding portion 12 into which the second bolt 230 is inserted to hold the second bolt 230 are formed, the holding plate material presses down the clamp member 10, the holding plate material is fixed to the first valve box block 110 and the first driving portion block 120 by the first bolt 130, the holding plate material presses down the clamp member 10, the holding plate material is fixed to the second valve box block 210 and the second driving portion block 220 by the second bolt 230, the valve structure further forms another first valve box bolt insertion hole 113, another first driving portion bolt fixing hole 123, another first bolt holding portion 11, another second valve box bolt insertion hole 213, another second driving portion bolt fixing hole 223, and another second bolt holding portion 12, the valve structure further comprises another first bolt 130 and another second bolt 230, one of the first bolts 130 is placed in one of the first valve box bolt insertion holes 113, one of the first driving portion bolt fixing holes 123, and one of the first bolt holding portions 11, the other first bolt 130 is placed in the other first valve box bolt insertion hole 113, the other first driving portion bolt fixing hole 123, and the other first bolt holding portion 11, one of the second bolts 230 is placed in one of the second valve box bolt insertion holes 213, one of the second driving portion bolt fixing holes 223, and one of the second bolt holding portions 12, and the other second bolt 230 is placed in the other second valve box bolt insertion hole 213, the other second driving portion bolt fixing hole 223, and the other second bolt holding portion 12.

According to an invention described in claim 4, in the valve structure of claim 2, a first flange portion 114 is formed in the first connecting port 111, a second flange portion 218a, 218b is formed in the second connecting port 211a, 211b, a first fixing portion 13 which abuts against the first flange portion 114 is formed between the pair of first bolt holding portions 11a, 11b, a second fixing portion 14 which abuts against the second flange portion 218a, 218b is formed between the pair of second bolt holding portions 12a, 12b, and the first flange portion 114 and the second flange portion 218a, 218b are located between the first fixing portion 13 and the second fixing portion 14 to fix the first connecting port 11 and the second connecting port 211a, 211b to each other.

According to an invention described in claim 5, in the valve structure of claim 4, the pair of first bolt holding portions 11a, 11b form a guider of the first flange portion 114, and the pair of second bolt holding portions 12a, 12b form a guider of the second flange portion 218a, 218b.

According to an invention described in claim 6, in the valve structure of claim 4, the first fixing portion 13 and the second fixing portion 14 are formed into arc shapes.

According to an invention described in claim 7, the valve structure of claim 4 further includes a second clamp member 51 which sandwiches the first flange portion 114 and the second flange portion 218a, 218b, wherein the first fixing portion 13 and the second fixing portion 14 are placed on one of sides of the first flange portion 114 and the second flange portion 218a, 218b, and the second clamp member 51 is placed on other sides of the first flange portion 114 and the second flange portion 218a, 218b.

According to an invention described in claim 8, in the valve structure of claim 2, a first valve box clamp-side abutting surface 115 is formed on one of the first valve box bolt insertion holes 113, a first valve box driving portion-side abutting surface 116 is formed on other first valve box bolt insertion hole 113, a first driving portion valve box-side abutting surface 125 is formed in an opening of the first driving portion bolt fixing hole 123, a first bolt head abutting surface 16 of the first bolt 130 is formed on one of the first bolt holding portions 11, a first bolt holding portion valve box-side abutting surface 17 is formed on other first bolt holding portion 11, a second valve box clamp-side abutting surface 215 is formed on one of the second valve box bolt insertion holes 213, a second valve box driving portion-side abutting surface 216 is formed on other second valve box bolt insertion hole 213, a second driving portion valve box-side abutting surface 225 is formed in an opening of the second driving portion bolt fixing hole 223, a second bolt head abutting surface of the second bolt 230 is formed on one of the second bolt holding portions 12, a second bolt holding portion valve box-side abutting surface 19 is formed on other second bolt holding portion 12, the first valve box clamp-side abutting surface 115 and the first bolt holding portion valve box-side abutting surface 17 are butted against each other, the first valve box driving portion-side abutting surface 116 and the first driving portion valve box-side abutting surface 125 are butted against each other, the second valve box clamp-side abutting surface 215 and the second bolt holding portion valve box-side abutting surface 19 are butted against each other, and the second valve box driving portion-side abutting surface 216 and the second driving portion valve box-side abutting surface 225 are butted against each other.

According to an invention described in claim 9, the valve structure of claim 1 further includes a first flow path port 117 projecting from the first valve box block 110, and a second flow path port 217 projecting from the second valve box block 210, wherein a first flow path port abutting surface 17a which abuts against the first flow path port 117, and a second flow path port abutting surface 19a which abuts against the second flow path port 217 are formed on the clamp member 10.

According to an invention described in claim 10, in the valve structure of claim 9, the first flow path port abutting surface 17a and the second flow path port abutting surface 19a are formed into arc shapes.

According to an invention described in claim 11, in the valve structure of claim 1, at least one of the first valve box block 110 and the second valve box block 210 includes a plurality of valve bodies A and a plurality of flow path ports respectively corresponding to the valve bodies A, and the first driving portion block 120 and the second driving portion block 220 include a plurality of valve body operating members 121, 221 respectively corresponding to the valve bodies A.

According to an invention described in claim 12, in the valve structure of claim 9, different medical liquids a, b, c are introduced into the first flow path port 117 and the second flow path port 217.

Effect of the Invention

According to the valve structure of the present invention, the clamp member can be used for fixing the first valve box block and the first driving portion block to each other and fixing the second valve box block and the second driving portion block to each other, and the first connecting port and the second connecting port can be fixed to each other by fixing the clamp member, the first valve box block and the first driving portion block to each other, and by fixing the clamp member, the second valve box block and the second driving portion block to each other.

BRIEF DESCRIPTION OF DRAWINGS

FIG. 1 is an exploded perspective view showing a valve structure according to an embodiment of the present invention;

FIG. 2 is a perspective view showing a valve box block and a clamp member which compose the valve structure;

FIG. 3 are front views showing the valve box block which composes the valve structure;

FIG. 4 are perspective views showing a mounting manner of a second clamp member which composes the valve structure;

FIG. 5 are perspective views for explaining an outer shape of the valve box block which composes the valve structure;

FIG. 6 is a perspective view for explaining outer shapes of a driving portion block and the clamp member which compose the valve structure;

FIG. 7 is a front view of the valve structure;

FIG. 8 is a partial sectional view for explaining an inner structure of the valve structure;

FIG. 9 is a diagram showing before and after fixing through bolts;

FIG. 10 is an exploded perspective view showing a valve structure according to another embodiment of the invention;

FIG. 11 is a perspective view showing a valve box block and a clamp member which compose the valve structure of the embodiment;

FIG. 12 is a perspective view for explaining outer shapes of a driving portion block and the clamp member which compose the valve structure of the embodiment; and FIG. 13 is a front view of the valve structure of the embodiment.

MODE FOR CARRYING OUT THE INVENTION

A first embodiment of the present invention provides a valve structure including: a first valve box block in which a first flow path is formed and a first valve body for opening and closing the first flow path is placed; a first driving portion block provided therein with a first valve body operating member which operates the first valve body; a second valve box block in which a second flow path is formed and a second valve body for opening and closing the second flow path is placed; a second driving portion block provided therein with a second valve body operating member which operates the second valve body; a first connecting port projecting from the first valve box block; and a second connecting port projecting from the second valve box block; in which the first flow path and the second flow path are brought into communication with each other by connecting the first connecting port and the second connecting port to each other, wherein a first valve box bolt insertion hole into which a first bolt is inserted is formed in the first valve box block, a first driving portion bolt fixing hole into which the first bolt is inserted to fix the first bolt is formed in the first driving portion block, a second valve box bolt insertion hole into which a second bolt is inserted is formed in the second valve box block, a second driving portion bolt fixing hole into which the second bolt is inserted to fix the second bolt is formed in the second driving portion block, the first valve box block and the first driving portion block are fixed to each other by the first bolt, the second valve box block and the second driving portion block are fixed to each other by the second bolt, and the first connecting port and the second connecting port are fixed to each other by a clamp member. According to this embodiment, the first bolt is inserted into the first valve box bolt insertion hole, the first bolt is fixed by the first driving portion bolt fixing hole, the second bolt is inserted into the second valve box bolt insertion hole, and the second bolt is fixed by the second driving portion bolt fixing hole. By this configuration, the first valve box block and the first driving portion block can be fixed to each other, the second valve box block and the second driving portion block can be fixed to each other, and the first connecting port and the second connecting port can be fixed to each other by the clamp member.

According to a second embodiment of the invention, in the valve structure of the first embodiment, a first bolt holding portion into which the first bolt is inserted to hold the first bolt, and a second bolt holding portion into which the second bolt is inserted to hold the second bolt are formed on the clamp member, the clamp member is fixed to the first valve box block and the first driving portion block by the first bolt, the clamp member is fixed to the second valve box block and the second driving portion block by the second bolt, the valve structure further forms another first valve box bolt insertion hole, another first driving portion bolt fixing hole, another first bolt holding portion, another second valve box bolt insertion hole, another second driving portion bolt fixing hole, and another second bolt holding portion, the valve structure further comprises another first bolt and another second bolt, one of the first bolts is placed in one of the first valve box bolt insertion holes, one of the first driving portion bolt fixing holes, and one of the first bolt holding portions, the other first bolt is placed in the other first valve box bolt insertion hole, the other first driving portion bolt fixing hole, and the other first bolt holding portion, one of the second bolts is placed in one of the second valve box bolt insertion holes, one of the second driving portion bolt fixing holes, and one of the second bolt holding portions, and the other second bolt is placed in the other second valve box bolt insertion hole, the other second driving portion bolt fixing hole, and the other second bolt holding portion. According to this embodiment, the clamp member is fixed to the first valve box block and the second valve box block. By this configuration, the first connecting port and the second connecting port can be fixed to each other. Therefore, the clamp member can be used for fixing the first valve box block and the first driving portion block to each other, and for fixing the second valve box block and the second driving portion block to each other. By fixing the clamp member, the first valve box block and the first driving portion block to each other, and by fixing the clamp member, the second valve box block and the second driving portion block to each other, the first connecting port and the second connecting port can be fixed to each other. By using the pair of first bolts and the pair of second bolts, the clamp member, the first valve box block and the first driving portion block can strongly be fixed to each other, the clamp member, the second valve box block and the second driving portion block can strongly be fixed to each other, and the first connecting port and the second connecting port can also be fixed to each other strongly.

According to a third embodiment of the invention, the valve structure of the first embodiment further includes a holding plate material where a first bolt holding portion into which the first bolt is inserted to hold the first bolt and a second bolt holding portion into which the second bolt is inserted to hold the second bolt are formed, the holding plate material presses down the clamp member, the holding plate material is fixed to the first valve box block and the first driving portion block by the first bolt, the holding plate material presses down the clamp member, the holding plate material is fixed to the second valve box block and the second driving portion block by the second bolt, the valve structure further forms ene mere another first valve box bolt insertion hole, another first driving portion bolt fixing hole, another first bolt holding portion, another second valve box bolt insertion hole, another second driving portion bolt fixing hole, and another second bolt holding portion, the valve structure further comprises another first bolt and another second bolt, one of the first bolts is placed in one of the first valve box bolt insertion holes, one of the first driving portion bolt fixing holes, and one of the first bolt holding portions, the other first bolt is placed in the other first valve box bolt insertion hole, the other first driving portion bolt fixing hole, and the other first bolt holding portion, one of the second bolts is placed in one of the second valve box bolt insertion holes, one of the second driving portion bolt fixing holes, and one of the second bolt holding portions, and the other second bolt is placed in the other second valve box bolt insertion hole, the other second driving portion bolt fixing hole, and the other second bolt holding portion. According to this embodiment, the holding plate material is fixed to the first valve box block and the second valve box block. According to this, the clamp member, the first valve box block and the first driving portion block can be fixed to each other, the clamp member, the second valve box block and the second driving portion block can be fixed to each other, and the first connecting port and the second connecting port can be fixed to each other. Further, by using the pair of first bolts and the pair of second bolts, the clamp member, the first valve box block and the first driving portion block can strongly be fixed to each other, the clamp member, the second valve box block and the second driving portion block can strongly be fixed to each other, and the first connecting port and the second connecting port can also be fixed to each other strongly.

According to a fourth embodiment of the invention, in the valve structure of the second embodiment, a first flange portion is formed in the first connecting port, a second flange portion is formed in the second connecting port, a first fixing portion which abuts against the first flange portion is formed between the pair of first bolt holding portions, a second fixing portion which abuts against the second flange portion is formed between the pair of second bolt holding portions, and the first flange portion and the second flange portion are located between the first fixing portion and the second fixing portion to fix the first connecting port and the second connecting port to each other. According to this embodiment, since the first flange portion and the second flange portion are sandwiched between the first fixing portion and the second fixing portion, it is possible to strongly fix.

According to a fifth embodiment of the invention, in the valve structure of the fourth embodiment, the pair of first bolt holding portions form a guider of the first flange portion, and the pair of second bolt holding portions form a guider of the second flange portion. According to this embodiment, the pair of first bolt holding portions and the pair of second bolt holding portions become the guiders of the first flange portion and the second flange portion. According to this configuration, it becomes easy to guide the first flange portion and the second flange portion into between the first fixing portion and the second fixing portion.

According to a sixth embodiment of the invention, in the valve structure of the forth embodiment, the first fixing portion and the second fixing portion are formed into arc shapes. According to this embodiment, the first fixing portion and the second fixing portion can be placed along the first flange portion and the second flange portion.

According to a seventh embodiment of the invention, the valve structure of the fourth embodiment further includes a second clamp member which sandwiches the first flange portion and the second flange portion, wherein the first fixing portion and the second fixing portion are placed on one of sides of the first flange portion and the second flange portion, and the second clamp member is placed on other sides of the first flange portion and the second flange portion. According to this embodiment, by using the second clamp member, it is possible to more strongly fix.

According to an eighth embodiment of the invention, in the valve structure of the second embodiment, a first valve box clamp-side abutting surface is formed on one of the first valve box bolt insertion holes, a first valve box driving portion-side abutting surface is formed on other first valve box bolt insertion hole, a first driving portion valve box-side abutting surface is formed in an opening of the first driving portion bolt fixing hole, a first bolt head abutting surface of the first bolt is formed on one of the first bolt holding portions, a first bolt holding portion valve box-side abutting surface is formed on other first bolt holding portion, a second valve box clamp-side abutting surface is formed on one of the second valve box bolt insertion holes, a second valve box driving portion-side abutting surface is formed on other second valve box bolt insertion hole, a second driving portion valve box-side abutting surface is formed in an opening of the second driving portion bolt fixing hole, a second bolt head abutting surface of the second bolt is formed on one of the second bolt holding portions, a second bolt holding portion valve box-side abutting surface is formed on other second bolt holding portion, the first valve box clamp-side abutting surface and the first bolt holding portion valve box-side abutting surface are butted against each other, the first valve box driving portion-side abutting surface and the first driving portion valve box-side abutting surface are butted against each other, the second valve box clamp-side abutting surface and the second bolt holding portion valve box-side abutting surface are butted against each other, and the second valve box driving portion-side abutting surface and the second driving portion valve box-side abutting surface are butted against each other. According to this embodiment, the first valve box clamp-side abutting surface formed on one of the first valve box bolt insertion holes and the first bolt holding portion valve box-side abutting surface formed on the other first bolt holding portion are made to butt with each other, and the second valve box clamp-side abutting surface formed on one of the second valve box bolt insertion holes and the second bolt holding portion valve box-side abutting surface formed on the other second bolt holding portion are made to butt with each other. According to this configuration, the clamp member can strongly be fixed to the first valve box block and the second valve box block. Further, the first driving portion valve box-side abutting surface formed in the opening of the first driving portion bolt fixing hole and the first valve box driving portion-side abutting surface formed on the other first valve box bolt insertion hole formed on the other first valve box bolt insertion hole are made to butt with each other. According to this configuration, the first valve box block and the first driving portion block can strongly be fixed to each other. The second driving portion valve box-side abutting surface formed in the opening of the second driving portion bolt fixing hole and the second valve box bolt insertion hole formed in the other second valve box bolt insertion hole are made to butt with each other. According to this, the second valve box block and the second driving portion block can strongly be fixed to each other.

According to a ninth embodiment of the invention, the valve structure of the first embodiment further includes a first flow path port projecting from the first valve box block, and a second flow path port projecting from the second valve box block, wherein a first flow path port abutting surface which abuts against the first flow path port, and a second flow path port abutting surface which abuts against the second flow path port are formed on the clamp member. According to this embodiment, since the clamp member includes the first flow path port abutting surface and the second flow path port abutting surface, the clamp member can be fixed to the first valve box block and the second valve box block more strongly. By forming the first flow path port abutting surface and the second flow path port abutting surface are formed, a width of the clamp member can be reduced. Therefore, it becomes easy bring the first valve box block and the second valve box block proximately to each other, and since the first valve box block and the second valve box block are placed proximately to each other, the first connecting port and the second connecting port can be made short.

According to a tenth embodiment of the invention, in the valve structure of the ninth embodiment, the first flow path port abutting surface and the second flow path port abutting surface are formed into arc shapes. According to this embodiment, the first flow path port abutting surface and the second flow path port abutting surface can be placed along the first flow path port and the second flow path port.

According to an eleventh embodiment of the invention, in the valve structure of the first embodiment, at least one of the first valve box block and the second valve box block includes a plurality of valve bodies and a plurality of flow path ports respectively corresponding to the valve bodies, and the first driving portion block and the second driving portion block include a plurality of valve body operating members respectively corresponding to the valve bodies. According to this embodiment, since the plurality of flow path ports are provided, different medical liquids can be introduced for example.

According to a twelfth embodiment of the invention, in the valve structure of the ninth embodiment, different medical liquids are introduced into the first flow path port and the second flow path port. According to this embodiment, since different medical liquids can be introduced in a switching manner, the present invention is suitable for a substrate processing device.

EMBODIMENTS

A valve structure according to an embodiment of the present invention will be described below.

FIG. 1 is an exploded perspective view showing a valve structure according to an embodiment, FIG. 2 is a perspective view showing a valve box block and a clamp member which compose the valve structure of the embodiment, FIG. 3 is a front view showing the valve box block which composes the valve structure of the embodiment, FIG. 4 is a perspective view showing a mounting manner of a second clamp member which composes the valve structure of the embodiment, FIG. 5 is a perspective view for explaining an outer shape of the valve box block which composes the valve structure of the embodiment, FIG. 6 is a perspective view for explaining outer shapes of a driving portion block and the clamp member which compose the valve structure of the embodiment, FIG. 7 is a front view of the valve structure of the embodiment, FIG. 8 is a partial sectional view for explaining an inner structure of the valve structure of the embodiment, and FIG. 9 is a diagram showing before and after fixing through bolts.

The valve structure according to the embodiment includes a first valve box block 110 provided therein with a first valve body A (see FIG. 8), a first driving portion block 120 provided therein with a first valve body operating member 121 which operates the first valve body A, a second valve box block 210 provided therein with a second valve body A (see FIG. 8), a second driving portion block 220 provided therein with a second valve body operating member 221 which operates the second valve body A, and a clamp member 10 which connects the first valve box block 110, the first driving portion block 120, the second valve box block 210 and the second driving portion block 220 to each other.

The valve structure shown in FIG. 1 further includes a third valve box block 310 provided therein with a third valve body A (see FIG. 8), a third driving portion block 320 provided therein with a third valve body operating member 321 which operates the third valve body A, and a clamp member 20 which connects the second valve box block 210, the second driving portion block 220, the third valve box block 310 and the third driving portion block 320 to each other.

The first valve box block 110 includes a first connecting port 111 projecting from the first valve box block 110, the second valve box block 210 includes second connecting ports 211a and 211b projecting from the second valve box block 210, and the third valve box block 310 includes a third connecting port 311 projecting from the third valve box block 310.

As shown in FIG. 2, a first flow path 112 is formed in the first valve box block 110, a second flow path 212 is formed in the second valve box block 210, and a third flow path 312 is formed in the third valve box block 310.

The first flow path 112 is opened and closed by the first valve body A, the second flow path 212 is opened and closed by the second valve body A, and the third flow path 312 is opened and closed by the third valve body A.

The first flow path 112 and the second flow path 212 are brought into communication with each other by connecting the first connecting port 111 and the second connecting port 211a to each other, and the second flow path 212 and the third flow path 312 are brought into communication with each other by connecting the second connecting port 211b and the third connecting port 311 to each other.

First valve box bolt insertion holes 113 into which first bolts 130 are inserted is formed in the first valve box block 110. As the first valve box bolt insertion holes 113, a pair of first valve box bolt insertion holes 113a and 113b are formed. First bolts 130a and 130b as the first bolt 130 are inserted into the pair of first valve box bolt insertion holes 113a and 113b. In a state where the first bolts 130a and 130b are inserted into the pair of first valve box bolt insertion holes 113a and 113b, the first bolts 130a and 130b are placed on both sides of the first connecting port 111.

First driving portion bolt fixing holes 123 are formed in the first driving portion block 120. The first bolt 130 is inserted into the first driving portion bolt fixing hole 123 to fix the first bolt 130. A pair of first driving portion bolt fixing holes 123a and 123b are formed as the first driving portion bolt fixing hole 123. The first bolts 130a and 130b are inserted into and fixed to the pair of first driving portion bolt fixing holes 123a and 123b, respectively.

One of second valve box bolt insertion holes 213 into which one of second bolts 230 is inserted is formed in the second valve box block 210. As one of the second valve box bolt insertion holes 213, one of the pair of second valve box bolt insertion holes 213a and 213b is formed. One of second bolts 230a and 230b is inserted into one of the pair of second valve box bolt insertion holes 213a and 213b as one of the second bolts 230. In a state where one of the second bolts 230a and 230b is inserted into one of the pair of second valve box bolt insertion holes 213a and 213b, the second bolts 230a and 230b are placed on both sides of the second connecting port 211a.

One of the second driving portion bolt fixing holes 223 is formed in one of the second bolts 230. One of the second bolts 230 is inserted into the second driving portion bolt fixing holes 223 to fix one of the second bolts 230. One of a pair of second driving portion bolt fixing holes 223a and 223b is formed as one of the second driving portion bolt fixing holes 223. One of the second bolts 230a and 230b is inserted into and fixed to one of the pair of second driving portion bolt fixing holes 223a and 223b.

The other second valve box bolt insertion hole 214 into which the other second bolt 240 is inserted is formed in the second valve box block 210. As the other second valve box bolt insertion hole 214, the other one of pair of second valve box bolt insertion holes 214a and 214b is formed. Other one of second bolts 240a and 240b is inserted into the other one of the pair of second valve box bolt insertion holes 214a and 214b as the other second bolt 240. In a state where the other one of the second bolts 240a and 240b is inserted into the other one of the pair of second valve box bolt insertion holes 214a and 214b, the second bolts 240a and 240b are placed on both sides of the second connecting port 211b.

Other second driving portion bolt fixing hole 224 is formed in the second driving portion block 220. The other second bolt 240 is inserted into the other second driving portion bolt fixing hole 224 to fix the other second bolt 240. As the other second driving portion bolt fixing hole 224, the other one of the pair of second driving portion bolt fixing holes 224a and 224b is formed. The other one of the second bolts 240a and 240b is inserted into and fixed to the other one of the pair of second driving portion bolt fixing holes 224a and 224b.

Third valve box bolt insertion holes 313 into which third bolts 330 are inserted are formed in the third valve box block 310. A pair of third valve box bolt insertion holes 313a and 313b are formed as the third valve box bolt insertion holes 313. Third bolts 330a and 330b are inserted into the pair of third valve box bolt insertion holes 313a and 313b as the third bolts 330. In a state where the third bolts 330a and 330b are inserted into the pair of third valve box bolt insertion holes 313a and 313b, the third bolts 330a and 330b are placed on both sides of the second connecting port 211b.

Third driving portion bolt fixing holes 323 into which third bolts 330 are inserted to fix the third bolts 330 are formed in the third driving portion block 320. A pair of third driving portion bolt fixing holes 323a and 323b are formed as the third driving portion bolt fixing holes 323. The third bolts 330a and 330b are inserted into and fixed to the pair of third driving portion bolt fixing holes 323a and 323b, respectively.

The one clamp member 10 fixes the first connecting port 111 and the second connecting port 211a to each other. When fixing these ports to each other, it is preferable that the clamp member 10 is press-fitted into the first connecting port 111 and the second connecting port 211a, and pressure of contacted surfaces of the first connecting port 111 and the second connecting port 211a is held by the clamp member 10. It is preferable that the first connecting port 111 and the second connecting port 211a are press-fitted using a gasket.

First bolt holding portions 11 and second bolt holding portions 12 are formed on the one clamp member 10. The first bolts 130 are inserted into the first bolt holding portions 11 to hold the first bolts 130, and second bolts 230 are inserted into the second bolt holding portions 12 to hold the second bolts 230.

A pair of first bolt holding portions 11a and 11b are formed as the first bolt holding portions 11. The first bolts 130a and 130b are inserted into the pair of first bolt holding portions 11a and 11b, respectively. In a state where the clamp member 10 is mounted on the first valve box block 110 by the first bolts 130a and 130b, the pair of first bolt holding portions 11a and 11b are placed on both sides of the first connecting port 111.

A pair of second bolt holding portions 12a and 12b are formed as the second bolt holding portions 12. The one second bolts 230a and 230b are inserted into the par of second bolt holding portions 12a and 12b, respectively. In a state where the clamp member 10 is mounted on the second valve box block 210 by the one second bolts 230a and 230b, the pair of second bolt holding portions 12a and 12b are placed on both sides of the second connecting port 211a.

The one clamp member 10, the first valve box block 110 and the first driving portion block 120 are fixed to one another by the first bolt 130, and the one clamp member 10, the second valve box block 210 and the second driving portion block 220 are fixed to one another by the one second bolt 230.

The other clamp member 20 fixes the second connecting port 211b and the third connecting port 311 to each other. When fixing these ports to each other, it is preferable that the clamp member 20 is press-fitted into the second connecting port 211b and the third connecting port 311, and pressure of contacted surfaces of the second connecting port 211b and the third connecting port 311 is held by the clamp member 20. It is preferable that the second connecting port 211b and the third connecting port 311 are press-fitted using a gasket.

Second bolt holding portions 21 and third bolt holding portions 22 are formed on the other clamp member 20. The other second bolts 240 are inserted into the second bolt holding portions 21 to hold the other second bolts 240, and the third bolts 330 are inserted into the third bolt holding portions 22 to hold the third bolts 330.

A pair of second bolt holding portions 21a and 21b are formed as the second bolt holding portions 21. The other second bolts 240a and 240b are inserted into the pair of second bolt holding portions 21a and 21b, respectively. In a state where the other clamp member 20 is mounted on the second valve box block 210 by the other second bolts 240a and 240b, the pair of second bolt holding portions 21a and 21b are placed on both sides of the second connecting port 211b.

A pair of third bolt holding portions 22a and 22b are formed as the third bolt holding portions 22. The third bolts 330a and 330b are inserted into the pair of third bolt holding portions 22a and 22b, respectively. In a state where the other clamp member 20 is mounted on the third valve box block 310 by the third bolts 330a and 330b, the pair of third bolt holding portions 22a and 22b are placed on both sides of the third connecting port 311.

As described above, the other clamp member 20, the second valve box block 210 and the second driving portion block 220 are fixed to one another by the other second bolts 240, and the other clamp member 20, the third valve box block 310 and the third driving portion block 320 are fixed to one another by the third bolts 330.

FIG. 3(a) shows three valve box blocks, and FIG. 3(b) shows a state where connecting ports of these valve box blocks are press-fitted and connected to each other.

As shown in FIGS. 3, a first flange portion 114 is formed on the first connecting port 111, a second flange portion 218a is formed on the second connecting port 211a, a second flange portion 218b is formed on the second connecting port 211b, and a third flange portion 314 is formed on the third connecting port 311.

On the other hand, as shown in FIGS. 1 and 2, a first fixing portion 13 which abuts against the first flange portion 114 is formed on the one clamp member 10 between the pair of first bolt holding portions 11a and 11b, and a second fixing portion 14 which abuts against the second flange portion 218a is formed on the one clamp member 10 between the pair of second bolt holding portions 12a and 12b.

A second fixing portion 23 which abuts against the second flange portion 218b is formed on the other clamp member 20 between the pair of second bolt holding portions 21a and 21b, and a third fixing portion 24 which abuts against the third flange portion 314 is formed on the other clamp member 20 between the pair of third bolt holding portions 22a and 22b.

The one clamp member 10 locates the first flange portion 114 and the second flange portion 218a between the first fixing portion 13 and the second fixing portion 14, thereby fixing the first connecting port 111 and the second connecting port 211a to each other.

Since the one clamp member 10 sandwiches the first flange portion 114 and the second flange portion 218a by the first fixing portion 13 and the second fixing portion 14 in this manner, they can be fixed to each other strongly.

The first fixing portion 13 and the second fixing portion 14 are formed into arc shapes. By forming the first fixing portion 13 and the second fixing portion 14 into the arc shapes, the first fixing portion 13 and the second fixing portion 14 can be placed along the first flange portion 114 and the second flange portion 218a.

The pair of first bolt holding portions 11a and 11b form a guider of the first flange portion 114, and the pair of second bolt holding portions 12a and 12b form a guider of the second flange portion 218a.

The pair of first bolt holding portions 11a and 11b and the pair of second bolt holding portions 12a and 12b become guiders of the first flange portion 114 and the second flange portion 218a in this manner, it becomes easy to guide the first flange portion 114 and the second flange portion 218a in between the first fixing portion 13 and the second fixing portion 14.

The other clamp member 20 locates the second flange portion 218b and a third flange portion 314a between the second fixing portion 23 and the third fixing portion 24, thereby fixing the second connecting port 211b and the third connecting port 311 to each other.

Since the other clamp member 20 sandwiches the second flange portion 218b and the third flange portion 314 by the second fixing portion 23 and the third fixing portion 24 in this manner, they can be fixed to each other strongly.

The second fixing portion 23 and the third fixing portion 24 are formed into arc shapes. By forming the second fixing portion 23 and the third fixing portion 24 into the arc shapes, the second fixing portion 23 and the third fixing portion 24 can be placed along the second flange portion 218a and the third flange portion 314.

The pair of second bolt holding portions 21a and 21b form a guider of the second flange portion 218b, and the pair of third bolt holding portions 22a and 22b form a guider of the third flange portion 314.

The pair of second bolt holding portions 21a and 21b and the pair of third bolt holding portions 22a and 22b become the guiders of the second flange portion 218b and the third flange portion 314, it becomes easy to guide the second flange portion 218b and the third flange portion 314 in between the second fixing portion 23 and the third fixing portion 24.

In this embodiment, the first connecting port 111 is press-fitted into and connected to the second connecting port 211a using the first connecting port 111 as a male type and second connecting port 211a as a female type, and the second connecting port 211b is press-fitted into and connected to the third connecting port 311 using the second connecting port 211b as a male type and a third connecting port 311a as a female type. Alternatively, the first connecting port 111, the second connecting ports 211a and 211b and the third connecting port 311 may be formed into the same shapes, and they may be press-fitted and connected using gaskets.

FIG. 4 (a) shows a state where connecting portions of the valve box blocks are press-fitted into and connected to each other, and FIG. 4 (b) shows a state where the second clamp member is mounted on the valve box blocks whose connecting portions are press-fitted into and connected to each other.

As shown in FIGS. 1 and 4, it is preferable that a second clamp member 51 which sandwiches the first flange portion 114 and the second flange portion 218a, and a second clamp member 52 which sandwiches the second flange portion 218b and the third flange portion 314 are provided.

As shown in FIG. 4(a), the second clamp members 51 and 52 are mounted on the first flange portion 114, the second flange portions 218a and 218b and the third flange portion 314 from front and then, the second clamp members 51 and 52 are moved to upper positions along the first flange portion 114, the second flange portions 218a and 218b and the third flange portion 314 as shown in FIG. 4(b).

It is preferable that the second clamp members 51 and 52 are press-fitted into the first flange portion 114, the second flange portions 218a and 218b and the third flange portion 314, and pressure of contacted surfaces of the first flange portion 114 and the second flange portion 218a and pressure of contacted surfaces of the second flange portion 218b and the third flange portion 314 are held by the second clamp members 51 and 52.

The first fixing portion 13, the second fixing portions 14 and 23 and the third fixing portion 24 are placed on the first flange portion 114, the second flange portions 218a and 218b and the third flange portion 314 from below.

Therefore, the first fixing portion 13, the second fixing portions 14 and 23 and the third fixing portion 24 can be placed on one of sides of the first flange portion 114, the second flange portions 218a and 218b and the third flange portion 314, and the second clamp members 51 and 52 can be placed on the other sides of the first flange portion 114, the second flange portions 218a and 218b and the third flange portion 314, and the second clamp members 51 and 52 are used in addition to the clamp members 10 and 20. According to this configuration, they can be fixed more strongly.

An outer shape of the valve box block will be described below using FIG. 5.

As shown in FIG. 5(a), the first valve box block 110 forms a first valve box clamp-side abutting surface 115 in one of the first valve box bolt insertion holes 113, the second valve box block 210 forms a second valve box clamp-side abutting surface 215 in one of the second valve box bolt insertion holes 213 and one of the second valve box bolt insertion holes 214, and the third valve box block 310 forms a third valve box clamp-side abutting surface 315 in one of the third valve box bolt insertion holes 313.

As shown in FIG. 5(b), the first valve box block 110 forms a first valve box driving portion-side abutting surface 116 in the other first valve box bolt insertion hole 113, the second valve box block 210 forms a second valve box driving portion-side abutting surface 216 in the other second valve box bolt insertion hole 213 and the other second valve box bolt insertion hole 214, and the third valve box block 310 forms a third valve box driving portion-side abutting surface 316 in the other third valve box bolt insertion hole 313.

The first valve box block 110 includes a first flow path port 117 projecting from the first valve box block 110, the second valve box block 210 includes a second flow path port 217 projecting from the second valve box block 210, and the third valve box block 310 includes a third flow path port 317 projecting from the third valve box block 310.

An outer shape of the driving portion block and an outer shape of the clamp member will be described below using FIG. 6.

The first driving portion block 120 forms a first driving portion valve box-side abutting surface 125 on openings of the first driving portion bolt fixing holes 123, the second driving portion block 220 forms a second driving portion valve box-side abutting surface 225 on an opening of one of the second driving portion bolt fixing holes 223, and the third driving portion block 320 forms a third driving portion valve box-side abutting surface 325 on openings of the third driving portion bolt fixing holes 323.

The one clamp member 10 forms a first bolt head abutting surface 16 of one of the first bolts 130 on one of the first bolt holding portions 11, a first bolt holding portion valve box-side abutting surface 17 on the other first bolt holding portion 11, a second bolt head abutting surface 18 of one of the second bolts 230 on one of the second bolt holding portions 12, and a second bolt holding portion valve box-side abutting surface 19 on the other second bolt holding portion 12.

The other clamp member 20 forms a second bolt head abutting surface 26 of the other second bolt 240 on one of the second bolt holding portions 21, a second bolt holding portion valve box-side abutting surface 27 on the other second bolt holding portion 21, a third bolt head abutting surface 28 of the third bolt 330 on one of the third bolt holding portions 22, and a third bolt holding portion valve box-side abutting surface 29 on the other third bolt holding portion 22.

The one clamp member 10 forms a first flow path port abutting surface 17a which abuts against the first flow path port 117, and a second flow path port abutting surface 19a which abuts against the second flow path port 217. The other clamp member 20 forms a second flow path port abutting surface 27a which abuts against the second flow path port 217, and a third flow path port abutting surface 29a which abuts against the third flow path port 317.

The first flow path port abutting surface 17a, the second flow path port abutting surface 19a, the second flow path port abutting surface 27a and the third flow path port abutting surface 29a are formed into arc shapes such that they abut against outer peripheral surfaces of the first flow path port 117, the second flow path port 217 and the third flow path port 317.

In this embodiment, the first bolt head abutting surface 16 and the second bolt head abutting surface 18 are formed as flat surfaces having the same height, the first bolt holding portion valve box-side abutting surfaces 17 and the second bolt holding portion valve box-side abutting surfaces 19 are formed as flat surfaces having the same height, the second bolt head abutting surface 26 and the third bolt head abutting surface 28 are formed as flat surfaces having the same height, and the second bolt holding portion valve box-side abutting surfaces 27 and the third bolt holding portion valve box-side abutting surfaces 29 are formed as flat surfaces having the same height.

Butting of the valve box block, the driving portion block and the clamp member will be described below using FIG. 7.

The first valve box block 110 and the first driving portion block 120 are butted against the first valve box driving portion-side abutting surface 116 and the first driving portion valve box-side abutting surface 125, the second valve box block 210 and the second driving portion block 220 are butted against the second valve box driving portion-side abutting surface 216 and the second driving portion valve box-side abutting surface 225, and the third valve box block 310 and the third driving portion block 320 are butted against the third valve box driving portion-side abutting surface 316 and the third driving portion valve box-side abutting surface 325.

The one clamp member 10 and the first valve box block 110 are butted against the first bolt holding portion valve box-side abutting surfaces 17 and the first valve box clamp-side abutting surface 115, and the one clamp member 10 and the second valve box block 210 are butted against the second bolt holding portion valve box-side abutting surfaces 19 and the second valve box clamp-side abutting surface 215.

The other clamp member 20 and the second valve box block 210 are butted against the second bolt holding portion valve box-side abutting surface 27 ad the second valve box clamp-side abutting surface 215, and the other clamp member 20 and the third valve box block 310 are butted against the third bolt holding portion valve box-side abutting surfaces 29 and the third valve box clamp-side abutting surface 315.

The first flow path port abutting surface 17a of the one clamp member 10 is butted against the first flow path port 117, and the second flow path port abutting surface 19a of the one clamp member 10 is butted against the second flow path port 217. The second flow path port abutting surface 27a of the other clamp member 20 is butted against the second flow path port 217, and the third flow path port abutting surface 29a of the other clamp member 20 is butted against the third flow path port 317.

By butting the first valve box clamp-side abutting surface 115 and the first bolt holding portion valve box-side abutting surfaces 17 against each other and by butting the second valve box clamp-side abutting surface 215 and the second bolt holding portion valve box-side abutting surfaces 19 against each other as described above, the one clamp member 10 can strongly be fixed to the first valve box block 110 and the second valve box block 210.

Similarly, by butting the second valve box clamp-side abutting surface 215 and the second bolt holding portion valve box-side abutting surfaces 27 against each other and by butting the third valve box clamp-side abutting surface 315 and the third bolt holding portion valve box-side abutting surfaces 29 against each other, the other clamp member 20 can strongly be fixed to the second valve box block 210 and the third valve box block 310.

Further, by butting the first driving portion valve box-side abutting surface 125 and the first valve box driving portion-side abutting surface 116 against each other, the first valve box block 110 and the first driving portion block 120 can strongly be fixed to each other.

Similarly, by butting the second driving portion valve box-side abutting surface 225 and the second valve box driving portion-side abutting surface 216 against each other, the second valve box block 210 and the second driving portion block 220 can strongly be fixed to each other.

Similarly, by butting the third driving portion valve box-side abutting surface 325 and the third valve box driving portion-side abutting surface 316 against each other, the third valve box block 310 and the third driving portion block 320 can strongly be fixed to each other.

Further, since the one clamp member 10 includes the first flow path port abutting surface 17a and the second flow path port abutting surface 19a, the one clamp member 10 can be fixed to the first valve box block 110 and the second valve box block 210 more strongly. By forming the first flow path port abutting surface 17a and the second flow path port abutting surface 19a, a width of the clamp member 10 can be narrowed. Therefore, it is easy to bring the first valve box block 110 and the second valve box block 210 close to each other. By bringing the first valve box block 110 and the second valve box block 210 close to each other, the first connecting port 111 and the second connecting port 211a can be shortened.

Similarly, since the other clamp member 20 includes the second flow path port abutting surface 27a and the third flow path port abutting surface 29a, the other clamp member 20 can be fixed to the second valve box block 210 and the third valve box block 310 more strongly. By forming the second flow path port abutting surface 27a and the third flow path port abutting surface 29a, a width of the clamp member 20 can be narrowed. Therefore, it is easy to bring the second valve box block 210 and the third valve box block 310 close to each other. By bringing the second valve box block 210 and the third valve box block 310 close to each other, the second connecting port 211b and the third connecting port 311 can be shortened.

As shown in FIG. 8, any driving methods can be employed for a first driving portion block 120A, a second driving portion block 220A and a third driving portion block 320A such as an electromagnetic valve method, an air operation valve method and a manual operation method. Valve bodies A corresponding to the respective driving methods are placed in a first valve box block 110A, a second valve box block 210A and a third valve box block 310A.

As shown in FIG. 9, medical liquid a is introduced into the first flow path port 117, medical liquid b is introduced into the second flow path port 217, medical liquid c is introduced into the third flow path port 317, and these medical liquids a, b and c are switched and derived as processing liquid. According to this, the valve structure can be used as a substrate processing device.

The first valve box block 110, the second valve box block 210 and the third valve box block 310 have one valve body A in this embodiment, but a plurality of valve bodies A and a plurality of flow path ports corresponding to these valve bodies A may be provided.

As described above, according to this embodiment, the first bolt 130 is inserted into the first valve box bolt insertion hole 113 and is held by the first bolt holding portion 11, the first bolt 130 is fixed by the first driving portion bolt fixing hole 123, the second bolt 230 is inserted into the second valve box bolt insertion hole 213 and is held by the second bolt holding portion 12, and the second bolt 230 is fixed by the second driving portion bolt fixing hole 223. According to this, the first valve box block 110 and the first driving portion block 120 can be fixed to each other, the second valve box block 210 and the second driving portion block 220 can be fixed to each other, and the clamp member 10 can be fixed to the first valve box block 110 and the second valve box block 210. By fixing the clamp member 10 to the first valve box block 110 and the second valve box block 210, the first connecting port 111 and the second connecting port 211a can be fixed to each other. Therefore, the clamp member 10 can be used for fixing the first valve box block 110 and the first driving portion block 120 to each other and for fixing the second valve box block 210 and the second driving portion block 220 to each other. The first connecting port 111 and the second connecting port 211a can be fixed to each other by fixing the clamp member 10, the first valve box block 110 and the first driving portion block 120 to each other, and by fixing the clamp member 10, the second valve box block 210 and the second driving portion block 220 to each other.

Similarly, the second bolt 240 is inserted into the second valve box bolt insertion hole 214 and is held by the second bolt holding portion 21, the second bolt 240 is fixed to the other second driving portion bolt fixing hole 224, the third bolt 330 is inserted into the third valve box bolt insertion hole 313 and is held by the third bolt holding portion 22, and the third bolt 330 is fixed by the third driving portion bolt fixing holes 323. According to this, the second valve box block 210 and the second driving portion block 220 can be fixed to each other, the third valve box block 310 and the third driving portion block 320 can be fixed to each other, and the clamp member 20 can be fixed to the second valve box block 210 and the third valve box block 310. The second connecting port 211b and the third connecting port 311 can be fixed to each other by fixing the clamp member 20 to the second valve box block 210 and the third valve box block 310. Therefore, the clamp member 20 can be used for fixing the second valve box block 210 and the second driving portion block 220 to each other and for fixing the third valve box block 310 and the third driving portion block 320 to each other. The second connecting port 211b and the third connecting port 311 can be fixed to each other by fixing the clamp member 20, the second valve box block 210 and the second driving portion block 220 to each other and by fixing the clamp member 20, the third valve box block 310 and the third driving portion block 320 to each other.

According to this embodiment, by using the pair of first bolts 130 and the pair of second bolts 230, it is possible to strongly fix the clamp member 10, the first valve box block 110 and the first driving portion block 120 to each other, and to strongly fix the clamp member 10, the second valve box block 210 and the second driving portion block 220 to each other, and it is also possible to strongly fix the first connecting port 111 and the second connecting port 211a to each other.

Similarly, by using the pair of second bolts 240 and the pair of third bolts 330, it is possible to strongly fix the clamp member 20, the second valve box block 210 and the second driving portion block 220 to each other, and to strongly fix the clamp member 20, the third valve box block 310 and the third driving portion block 320 to each other, and it is also possible to strongly fix the second connecting port 211b and the third connecting port 311 to each other.

A valve structure according to another embodiment of the present invention will be described below.

FIG. 10 is an exploded perspective view showing the valve structure according to this embodiment, FIG. 11 is a perspective view showing a valve box block and a clamp member which compose the valve structure of the embodiment, FIG. 12 is a perspective view for explaining outer shapes of a driving portion block and the clamp member which compose the valve structure of the embodiment, and FIG. 13 is a front view of the valve structure of the embodiment. The same symbols are allocated to the same function members as those of the previous embodiment, and description thereof will be omitted.

In this embodiment also, one clamp member 10 fixes a first connecting port 111 and a second connecting port 211a as shown in FIGS. 10 and 11. When fixing, it is preferable that the clamp member 10 is press-fitted into the first connecting port 111 and the second connecting port 211a, and pressure of contacted surfaces of the first connecting port 111 and the second connecting port 211a is held by the clamp member 10. It is preferable that the first connecting port 111 and the second connecting port 211a are press-fitted into each other using a gasket.

In this embodiment also, another clamp member 20 fixes a second connecting port 211b and a third connecting port 311 to each other. When fixing, it is preferable that the clamp member 20 is press-fitted into the second connecting port 211b and the third connecting port 311, and pressure of contacted surfaces of the second connecting port 211b and the third connecting port 311 is held by the clamp member 20. It is preferable that the second connecting port 211b and the third connecting port 311 are press-fitted into each other using a gasket.

In this embodiment, the following members are formed in a bolt head-contact surface member 60, i.e., first bolt holding portions 11 into which first bolts 130 are inserted to hold first bolts 130, second bolt holding portions 12 into which one second bolts 230 are inserted to hold one second bolts 230, second bolt holding portions 21 into which other second bolts 240 are inserted to hold another second bolts 240, and third bolt holding portions 22 into which third bolts 330 are inserted to hold third bolts 330.

One bolt head-contact surface member which forms the first bolt holding portions 11 and the second bolt holding portions 12, and another bolt head-contact surface member which forms the second bolt holding portions 21 and the third bolt holding portions 22 may compose the bolt head-contact surface member 60.

In this embodiment also, the one clamp member 10, a first valve box block 110 and a first driving portion block 120 are fixed to each other by the first bolts 130, and the one clamp member 10, a second valve box block 210 and a second driving portion block 220 are fixed to each other by the one second bolts 230.

The other clamp member 20, the second valve box block 210 and the second driving portion block 220 are fixed to each other by the other second bolts 240, and the other clamp member 20, a third valve box block 310 and a third driving portion block 320 are fixed to each other by the third bolts 330.

As shown in FIGS. 12 and 13, in this embodiment also, the first driving portion block 120 forms a first driving portion valve box-side abutting surface 125 on openings of first driving portion bolt fixing holes 123, the second driving portion block 220 forms a second driving portion valve box-side abutting surface 225 on openings of the one second driving portion bolt fixing holes 223, and the third driving portion block 320 forms a third driving portion valve box-side abutting surface 325 on openings of the third driving portion bolt fixing holes 323.

In this embodiment, the bolt head-contact surface member 60 forms a first bolt head abutting surface 16 of the first bolts 130 on one of the first bolt holding portions 11, a second bolt head abutting surface 18 of the one second bolts 230 on one of the second bolt holding portions 12, a second bolt head abutting surface 26 of the other second bolts 240 on one of the second bolt holding portions 21, and a third bolt head abutting surface 28 of the third bolts 330 on one of the third bolt holding portions 22.

The bolt head-contact surface member 60 forms a clamp member-side abutting surface 61 on the other first bolt holding portion 11, the other second bolt holding portion 12, the other second bolt holding portion 21, and the other third bolt holding portion 22.

In this embodiment, a bolt head-contact surface member-side abutting surface 15 is formed on one side of the one clamp member 10, and a first bolt holding portion valve box-side abutting surface 17 and a second bolt holding portion valve box-side abutting surface 19 are formed on the other side of the one clamp member 10.

In this embodiment, a bolt head-contact surface member-side abutting surface 25 is formed on one side of the other clamp member 20, and a second bolt holding portion valve box-side abutting surface 27 and a third bolt holding portion valve box-side abutting surface 29 are formed on the other side of the other clamp member 20.

In this embodiment also, the one clamp member 10 forms a first flow path port abutting surface 17a which abuts against the first flow path port 117, and a second flow path port abutting surface 19a which abuts against the second flow path port 217. The other clamp member 20 forms a second flow path port abutting surface 27a which abuts against the second flow path port 217, and a third flow path port abutting surface 29a which abuts against the third flow path port 317.

The first flow path port abutting surface 17a, the second flow path port abutting surface 19a, the second flow path port abutting surface 27a and the third flow path port abutting surface 29a are formed into arc shapes such that they abut against outer peripheral surfaces of the first flow path port 117, the second flow path port 217 and the third flow path port 317.

In this embodiment, the first bolt head abutting surface 16 and the second bolt head abutting surface 18 are formed as flat surfaces having the same height, the first bolt holding portion valve box-side abutting surface 17 and the second bolt holding portion valve box-side abutting surface 19 are formed as flat surfaces having the same height, the second bolt head abutting surface 26 and the third bolt head abutting surface 28 are formed as flat surfaces having the same height, and the second bolt holding portion valve box-side abutting surface 27 and the third bolt holding portion valve box-side abutting surface 29 are formed as flat surfaces having the same height.

As shown in FIG. 13, the first valve box block 110 and the first driving portion block 120 butt the first valve box driving portion-side abutting surface 116 and the first driving portion valve box-side abutting surface 125 against each other, the second valve box block 210 and the second driving portion block 220 butt the second valve box driving portion-side abutting surface 216 and the second driving portion valve box-side abutting surface 225 against each other, and the third valve box block 310 and the third driving portion block 320 butt the third valve box driving portion-side abutting surface 316 and the third driving portion valve box-side abutting surface 325 against each other.

The one clamp member 10 and the first valve box block 110 butt the first bolt holding portion valve box-side abutting surface 17 and the first valve box clamp-side abutting surface 115 against each other, and the one clamp member 10 and the second valve box block 210 butt the second bolt holding portion valve box-side abutting surface 19 and the second valve box clamp-side abutting surface 215 against each other.

The other clamp member 20 and the second valve box block 210 butt the second bolt holding portion valve box-side abutting surface 27 and the second valve box clamp-side abutting surface 215 against each other, and the other clamp member 20 and the third valve box block 310 butt the third bolt holding portion valve box-side abutting surface 29 and the third valve box clamp-side abutting surface 315 against each other.

The first flow path port abutting surface 17*a* of the one clamp member 10 butts against the first flow path port 117, and the second flow path port abutting surface 19*a* of the one clamp member 10 butts against the second flow path port 217. The second flow path port abutting surface 27*a* of the other clamp member 20 butts against the second flow path port 217, and the third flow path port abutting surface 29*a* of the other clamp member 20 butts against the third flow path port 317.

The first valve box clamp-side abutting surface 115 and the first bolt holding portion valve box-side abutting surface 17 are butted against each other and the second valve box clamp-side abutting surface 215 and the second bolt holding portion valve box-side abutting surface 19 are butted against each other in this manner. According to this, the one clamp member 10 can strongly be fixed to the first valve box block 110 and the second valve box block 210.

Similarly, the second valve box clamp-side abutting surface 215 and the second bolt holding portion valve box-side abutting surface 27 are butted against each other and the third valve box clamp-side abutting surface 315 and the third bolt holding portion valve box-side abutting surface 29 are butted against each other. According to this, the other clamp member 20 can strongly be fixed to the second valve box block 210 and the third valve box block 310.

Further, by butting the first driving portion valve box-side abutting surface 125 and the first valve box driving portion-side abutting surface 116 against each other, the first valve box block 110 and the first driving portion block 120 can strongly be fixed to each other.

Similarly, by butting the second driving portion valve box-side abutting surface 225 and the second valve box driving portion-side abutting surface 216 against each other, the second valve box block 210 and the second driving portion block 220 can strongly be fixed to each other.

Similarly, by butting the third driving portion valve box-side abutting surface 325 and the third valve box driving portion-side abutting surface 316 against each other, the third valve box block 310 and the third driving portion block 320 can strongly be fixed to each other.

Further, since the one clamp member 10 includes the first flow path port abutting surface 17*a* and the second flow path port abutting surface 19*a*, the one clamp member 10 can be fixed to the first valve box block 110 and the second valve box block 210 more strongly. Further, since the width of the clamp member 10 can be narrowed by forming the first flow path port abutting surface 17*a* and the second flow path port abutting surface 19*a*, it is easy to bring the first valve box block 110 and the second valve box block 210 close to each other. By bringing the first valve box block 110 and the second valve box block 210 close to each other, it is possible to shorten the first connecting port 111 and the second connecting port 211*a*.

Similarly, since the other clamp member 20 includes the second flow path port abutting surface 27*a* and the third flow path port abutting surface 29*a*, the other clamp member 20 can be fixed to the second valve box block 210 and the third valve box block 310 more strongly. Further, since the width of the clamp member 20 can be narrowed by forming the second flow path port abutting surface 27*a* and the third flow path port abutting surface 29*a*, it is easy to bring the second valve box block 210 and the third valve box block 310 close to each other. By bringing the second valve box block 210 and the third valve box block 310 close to each other, the second connecting port 211*b* and the third connecting port 311 can be shortened.

As described above, according to this embodiment, the first bolt 130 is inserted into the first valve box bolt insertion hole 113 and is held by the first bolt holding portion 11, the first bolt 130 is fixed by the first driving portion bolt fixing hole 123, the second bolt 230 is inserted into the second valve box bolt insertion hole 213 and is held by the second bolt holding portion 12, and the second bolt 230 is fixed by the second driving portion bolt fixing hole 223. According to this, the first valve box block 110 and the first driving portion block 120 can be fixed to each other, the second valve box block 210 and the second driving portion block 220 can be fixed to each other, and the clamp member 10 can be fixed to the first valve box block 110 and the second valve box block 210. The first connecting port 111 and the second connecting port 211*a* can be fixed to each other by fixing the clamp member 10 to the first valve box block 110 and the second valve box block 210. Therefore, the clamp member 10 and the bolt head-contact surface member 60 can be used for fixing the first valve box block 110 and the first driving portion block 120 to each other and for fixing the second valve box block 210 and the second driving portion block 220 to each other. BY fixing the clamp member 10, the first valve box block 110 and the first driving portion block 120 to each other and by fixing the clamp member 10, the second valve box block 210 and the second driving portion block 220 to each other, the first connecting port 111 and the second connecting port 211*a* can be fixed to each other.

Similarly, the second bolt 240 is inserted into the second valve box bolt insertion hole 214 and is held by the second bolt holding portion 21, the second bolt 240 is fixed by the other second driving portion bolt fixing hole 224, the third bolt 330 is inserted into the third valve box bolt insertion hole 313 and is held by the third bolt holding portion 22, and the third bolt 330 is fixed by the third driving portion bolt fixing holes 323. According to this, the second valve box block 210 and the second driving portion block 220 can be fixed to each other, the third valve box block 310 and the third driving portion block 320 can be fixed to each other, and the clamp member 20 can be fixed to the second valve box block 210 and the third valve box block 310. By fixing the clamp member 20 to the second valve box block 210 and the third valve box block 310, the second connecting port 211*b* and the third connecting port 311 can be fixed to each other. Therefore, the clamp member 20 and the bolt head-contact surface member 60 can be used for fixing the second valve box block 210 and the second driving portion block 220 to each other and for fixing the third valve box block 310 and the third driving portion block 320 to each other. By fixing the clamp member 20, the second valve box block 210 and the second driving portion block 220 to each other, and by fixing the clamp member 20, the third valve box block 310 and the third driving portion block 320 to each other, the second connecting port 211*b* and the third connecting port 311 can be fixed to each other.

Further, according to the embodiment, by using the pair of first bolts 130 and the pair of second bolts 230, it is possible to strongly fix the clamp member 10, the first valve box block 110 and the first driving portion block 120 to each other, and to strongly fix the clamp member 10, the second valve box block 210 and the second driving portion block 220 to each other, and the first connecting port 111 and the second connecting port 211a can also be fixed to each other strongly.

Similarly, by using the pair of second bolts 240 and the pair of third bolts 330, it is possible to strongly fix the clamp member 20, the second valve box block 210 and the second driving portion block 220 to each other, and to strongly fix the clamp member 20, the third valve box block 310 and the third driving portion block 320 to each other, and the second connecting port 211b and the third connecting port 311 can also be fixed to each other strongly.

INDUSTRIAL APPLICABILITY

According to the present invention, arbitrary number of valve box blocks and driving portion blocks can be connected to each other, and the invention is suitable for a semiconductor cleaning device which requires extremely high cleaning ability and quick switching ability of medical liquid.

EXPLANATION OF SYMBOLS 10, 20 clamp member
11, 11a, 11b first bolt holding portion
12, 12a, 12b, 21, 21a, 21b second bolt holding portion
13 first fixing portion
14, 23 second fixing portion
15 bolt head-contact surface member-side abutting surface
16 first bolt head abutting surface
17 first bolt holding portion valve box-side abutting surface
17a first flow path port abutting surface
18, 26 second bolt head abutting surface
19, 27 second bolt holding portion valve box-side abutting surface
19a, 27a second flow path port abutting surface
22, 22a, 22b third bolt holding portion
24 third fixing portion
25 bolt head-contact surface member-side abutting surface
28 third bolt head abutting surface
29 third bolt holding portion valve box-side abutting surface
29a third flow path port abutting surface
51, 52 second clamp member
60 bolt head-contact surface member
61 clamp member-side abutting surface
110 first valve box block
111 first connecting port
112 first flow path
113, 113a, 113b first valve box bolt insertion hole
114 first flange portion
115 first valve box clamp-side abutting surface
116 first valve box driving portion-side abutting surface
117 first flow path port
120, 120A first driving portion block
121 first valve body operating member
123, 123a, 123b first driving portion bolt fixing hole
125 first driving portion valve box-side abutting surface
130, 130a, 130b first bolt
210 second valve box block
211a, 211b second connecting port
212 second flow path
213, 213a, 213b, 214, 214a, 214b second valve box bolt insertion hole
215 second valve box clamp-side abutting surface
216 second valve box driving portion-side abutting surface
217 second flow path port
218a, 218b second flange portion
220, 220A second driving portion block
221 second valve body operating member
223, 223a, 223b, 224, 224a, 224b second driving portion bolt fixing hole
225 second driving portion valve box-side abutting surface
230, 230a, 230b, 240, 240a, 240b second bolt
310 third valve box block
311 third connecting port
312 third flow path
313, 313a, 313b third valve box bolt insertion hole
314 third flange portion
315 third valve box clamp-side abutting surface
316 third valve box driving portion-side abutting surface
317 third flow path port
320, 320A third driving portion block
321 third valve body operating member
323, 323a, 323b third driving portion bolt fixing hole
325 third driving portion valve box-side abutting surface
330, 330a, 330b third bolt
A valve body, first valve body, second valve body, third valve body
a, b, c medical liquid

The invention claimed is:

1. A valve structure comprising:
a first valve box block in which a first flow path is formed and a first valve body for opening and closing the first flow path is placed;
a first driving portion block provided therein with a first valve body operating member which operates the first valve body;
a second valve box block in which a second flow path is formed and a second valve body for opening and closing the second flow path is placed;
a second driving portion block provided therein with a second valve body operating member which operates the second valve body;
a first connecting port projecting from the first valve box block; and
a second connecting port projecting from the second valve box block; in which
the first flow path and the second flow path are brought into communication with each other by connecting the first connecting port and the second connecting port to each other, wherein
a first valve box bolt insertion hole into which a first bolt is inserted is formed in the first valve box block,
a first driving portion bolt fixing hole into which the first bolt is inserted to fix the first bolt is formed in the first driving portion block,
a second valve box bolt insertion hole into which a second bolt is inserted is formed in the second valve box block,
a second driving portion bolt fixing hole into which the second bolt is inserted to fix the second bolt is formed in the second driving portion block,
the first valve box block and the first driving portion block are fixed to each other by the first bolt,
the second valve box block and the second driving portion block are fixed to each other by the second bolt, and
the first connecting port of the first valve box block fixed to first driving portion block and the second connecting port of the second valve box block fixed to the second driving portion block are fixed to each other by a clamp member.

2. The valve structure according to claim 1, wherein
a first bolt holding portion into which the first bolt is inserted to hold the first bolt, and a second bolt holding portion into which the second bolt is inserted to hold the second bolt are formed on the clamp member,
the clamp member is fixed to the first valve box block and the first driving portion block by the first bolt,
the clamp member is fixed to the second valve box block and the second driving portion block by the second bolt,
the valve structure further forms another first valve box bolt insertion hole, another first driving portion bolt fixing hole, another first bolt holding portion, another second valve box bolt insertion hole, another second driving portion bolt fixing hole, and another second bolt holding portion,
the valve structure further comprises another first bolt and another second bolt,
one of the first bolts is placed in one of the first valve box bolt insertion holes, one of the first driving portion bolt fixing holes, and one of the first bolt holding portions,
the another first bolt is placed in the another first valve box bolt insertion hole, the another first driving portion bolt fixing hole, and the another first bolt holding portion,
one of the second bolts is placed in one of the second valve box bolt insertion holes, one of the second driving portion bolt fixing holes, and one of the second bolt holding portions, and
the another second bolt is placed in the another second valve box bolt insertion hole, the another second driving portion bolt fixing hole, and the another second bolt holding portion.

3. The valve structure according to claim 2, wherein
a first flange portion is formed in the first connecting port,
a second flange portion is formed in the second connecting port,
a first fixing portion which abuts against the first flange portion is formed between the pair of first bolt holding portions,
a second fixing portion which abuts against the second flange portion is formed between the pair of second bolt holding portions, and
the first flange portion and the second flange portion are located between the first fixing portion and the second fixing portion to fix the first connecting port and the second connecting port to each other.

4. The valve structure according to claim 3, wherein
the pair of first bolt holding portions form a guider of the first flange portion, and
the pair of second bolt holding portions form a guider of the second flange portion.

5. The valve structure according to claim 3, wherein
the first fixing portion and the second fixing portion are formed into arc shapes.

6. The valve structure according to claim 3, further comprising a second clamp member which sandwiches the first flange portion and the second flange portion, wherein
the first fixing portion and the second fixing portion are placed on one of sides of the first flange portion and the second flange portion, and
the second clamp member is placed on other sides of the first flange portion and the second flange portion.

7. The valve structure according to claim 2, wherein
a first valve box clamp-side abutting surface is formed on one of the first valve box bolt insertion holes,
a first valve box driving portion-side abutting surface is formed on other first valve box bolt insertion hole,
a first driving portion valve box-side abutting surface is formed in an opening of the first driving portion bolt fixing hole,
a first bolt head abutting surface of the first bolt is formed on one of the first bolt holding portions,
a first bolt holding portion valve box-side abutting surface is formed on other first bolt holding portion,
a second valve box clamp-side abutting surface is formed on one of the second valve box bolt insertion holes,
a second valve box driving portion-side abutting surface is formed on other second valve box bolt insertion hole,
a second driving portion valve box-side abutting surface is formed in an opening of the second driving portion bolt fixing hole,
a second bolt head abutting surface of the second bolt is formed on one of the second bolt holding portions,
a second bolt holding portion valve box-side abutting surface is formed on other second bolt holding portion,
the first valve box clamp-side abutting surface and the first bolt holding portion valve box-side abutting surface are butted against each other,
the first valve box driving portion-side abutting surface and the first driving portion valve box-side abutting surface are butted against each other,
the second valve box clamp-side abutting surface and the second bolt holding portion valve box-side abutting surface are butted against each other, and
the second valve box driving portion-side abutting surface and the second driving portion valve box-side abutting surface are butted against each other.

8. The valve structure according to claim 1, further comprising a holding plate material where a first bolt holding portion into which the first bolt is inserted to hold the first bolt and a second bolt holding portion into which the second bolt is inserted to hold the second bolt are formed, wherein
the holding plate material presses down the clamp member, the holding plate material is fixed to the first valve box block and the first driving portion block by the first bolt,
the holding plate material presses down the clamp member, the holding plate material is fixed to the second valve box block and the second driving portion block by the second bolt,
the valve structure further forms another first valve box bolt insertion hole, another first driving portion bolt fixing hole, another first bolt holding portion, another second valve box bolt insertion hole, another second driving portion bolt fixing hole, and another second bolt holding portion,
the valve structure further comprises another first bolt and another second bolt,
one of the first bolts is placed in one of the first valve box bolt insertion holes, one of the first driving portion bolt fixing holes, and one of the first bolt holding portions,
the another first bolt is placed in the another first valve box bolt insertion hole, the another first driving portion bolt fixing hole, and the another first bolt holding portion,
one of the second bolts is placed in one of the second valve box bolt insertion holes, one of the second driving portion bolt fixing holes, and one of the second bolt holding portions, and the another second bolt is placed in the another second valve box bolt insertion hole, the another second driving portion bolt fixing hole, and the another second bolt holding portion.

9. The valve structure according to claim 1, further comprising a first flow path port projecting from the first valve box block, and a second flow path port projecting from the second valve box block, wherein a first flow path port abutting surface which abuts against the first flow path port, and a second flow path port abutting surface which abuts against the second flow path port are formed on the clamp member.

10. The valve structure according to claim 9, wherein the first flow path port abutting surface and the second flow path port abutting surface are formed into arc shapes.

11. The valve structure according to claim 9, wherein wherein the first flow path port and the second flow path port receive different medical liquids.

12. The valve structure according to claim 1, wherein at least one of the first valve box block and the second valve box block includes a plurality of valve bodies and a plurality of flow path ports respectively corresponding to the valve bodies, and the first driving portion block and the second driving portion block include a plurality of valve body operating members respectively corresponding to the valve bodies.

* * * * *